United States Patent
Maddox (12)

(10) Patent No.: US 12,357,943 B2
(45) Date of Patent: Jul. 15, 2025

(54) COLLECTION AND SEPARATION SYSTEMS AND METHODS OF USE THEREOF AND ISOTOPE ANALYSIS SYSTEMS AND METHODS OF USE THEREOF

(71) Applicant: University of Georgia Research Foundation, Inc., Athens, GA (US)

(72) Inventor: Thomas Ronald Maddox, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 567 days.

(21) Appl. No.: 17/763,291

(22) PCT Filed: Sep. 24, 2020

(86) PCT No.: PCT/US2020/052384
§ 371 (c)(1),
(2) Date: Mar. 24, 2022

(87) PCT Pub. No.: WO2021/061904
PCT Pub. Date: Apr. 1, 2021

(65) Prior Publication Data
US 2022/0339580 A1     Oct. 27, 2022

Related U.S. Application Data

(60) Provisional application No. 62/967,697, filed on Jan. 30, 2020, provisional application No. 62/904,815, filed on Sep. 24, 2019.

(51) Int. Cl.
*B01D 53/02* (2006.01)
*B01D 53/50* (2006.01)
(Continued)

(52) U.S. Cl.
CPC .......... *B01D 53/75* (2013.01); *B01D 53/025* (2013.01); *B01D 53/504* (2013.01);
(Continued)

(58) Field of Classification Search
CPC ...... B01D 53/025; B01D 53/62; B01D 53/75; B01D 2257/50; B01D 2257/102; B01D 2257/302; B01D 2258/0283
(Continued)

(56) References Cited

U.S. PATENT DOCUMENTS 4,234,315 A * 11/1980 Scott ..................... G01N 31/12
                                                                     436/115
5,185,139 A * 2/1993 Krishnamurthy ... C01B 21/0466
                                                                      564/69

(Continued)

FOREIGN PATENT DOCUMENTS

| CN | 103499662 A | 1/2014 |
|---|---|---|
| GB | 2370517 A | 7/2002 |
| JP | H11-304784 A | 11/1999 |

OTHER PUBLICATIONS

Extended European Search Report for 20870154.0, mailed Sep. 25, 2023.
(Continued)

*Primary Examiner* — Minh Chau T Pham
(74) *Attorney, Agent, or Firm* — THOMAS | HORSTEMEYER, LLP

(57) ABSTRACT

Collection and separation systems, collection and separation methods, isotope analysis systems, methods of processing samples to analyze $^{15}N$, $^{13}C$, and $^{34}S$, and the like are provided. A system that includes a collection system in gaseous communication with a first device, wherein the collection system is configured to isolate two or more gases (Continued)

of a gaseous sample and configured to introduce each to a second device independently of one another is provided.

22 Claims, 8 Drawing Sheets

(51) Int. Cl.
 *B01D 53/56* (2006.01)
 *B01D 53/62* (2006.01)
 *B01D 53/75* (2006.01)
 *B01D 59/44* (2006.01)
(52) U.S. Cl.
 CPC ........... *B01D 53/565* (2013.01); *B01D 53/62* (2013.01); *B01D 2253/106* (2013.01); *B01D 2257/102* (2013.01); *B01D 2257/302* (2013.01); *B01D 2257/50* (2013.01); *B01D 2258/0283* (2013.01)
(58) Field of Classification Search
 USPC ............. 55/315; 564/69; 423/359; 62/24, 28
 See application file for complete search history.

(56) References Cited

U.S. PATENT DOCUMENTS

| | | | |
|---|---|---|---|
| 6,334,928 B1* | 1/2002 | Sekine | C23C 16/4412 118/724 |
| 6,649,129 B1 | 11/2003 | Neal | |
| 2009/0211213 A1* | 8/2009 | Tsuji | H01L 21/67109 55/442 |
| 2016/0320355 A1 | 11/2016 | Krummen et al. | |
| 2017/0336374 A1 | 11/2017 | Guzzonato et al. | |
| 2018/0076013 A1* | 3/2018 | Brodie | H01J 49/0468 |
| 2019/0272987 A1* | 9/2019 | Brodie | G01N 30/30 |

OTHER PUBLICATIONS

J. Potter, et al. "A gas-chromatograph, continuous flow-isotope ratio mass-spectrometry method for . . . and . . . measurement of complex fluid inclusion volatiles: Examples from the Khibina alkaline igneous complex, northwest Russia and the south Wales coalfields", Chemical Geology 244 (2007), pp. 186-201.

* cited by examiner

COLLECTION AND SEPARATION SYSTEMS AND METHODS OF USE THEREOF AND ISOTOPE ANALYSIS SYSTEMS AND METHODS OF USE THEREOF

CROSS-REFERENCE TO RELATED APPLICATION

This application is the 35 U.S.C. § 371 national stage of PCT application having serial number PCT/US2020/052384, filed on Sep. 24, 2020. This application also claims priority to U.S. provisional application entitled "ISOTOPE ANALYSIS SYSTEMS AND METHODS OF USE THEREOF," having Ser. No. 62/904,815 filed on Sep. 24, 2019, and also claims priority to U.S. provisional application entitled "SEPARATION SYSTEMS AND METHODS OF USE THEREOF AND ISOTOPE ANALYSIS SYSTEMS AND METHODS OF USE THEREOF," having Ser. No. 62/967,697 filed on Jan. 30, 2020, which is entirely incorporated herein by reference.

BACKGROUND

A well-known method of elemental analysis (C S) of organic compounds comprises the combustion analysis of a sample in a combustion zone at elevated temperatures, to ultimately produce carbon dioxide, nitrogen gas and sulfur dioxide. The resulting mixture of gases can be separated and analyzed using a detection device to determine the amount of each of carbon dioxide, nitrogen gas and sulfur dioxide. The presently known techniques suffer from various deficiencies: poor detection limits, use of large amounts of He, problems associated due to the presence of water, and the like.

SUMMARY

Embodiments of the present disclosure provide for collection and separation systems (also referred to as "collection system" or "separation system"), collection and separation methods, isotope analysis systems, methods of processing samples to analyze $^{15}N$, $^{13}C$, and $S^{34}$, and the like.

The present disclosure provides for a system, comprising: a collection system in gaseous communication with a first device, wherein the collection system is configured to isolate two or more gases of a gaseous sample and configured to introduce each to a second device independently of one another. In particular, the collection system is configured to isolate one or more of $CO_2$, $N_2$, and $SO_2$ (optionally two or more or optionally each of $CO_2$, $N_2$, and $SO_2$) of a gaseous sample and configured to introduce each of $CO_2$, $N_2$, and $SO_2$ to a second device independently of one another.

The collection system comprises a first valve, a second valve, a third valve, and fourth valve and a first trap, a second trap, and a third trap, wherein the first valve is configurable to be in gaseous communication with at least the second valve and a first device, wherein the second valve is configurable to be in gaseous communication with at least the first trap, the second trap, or the fourth valve, wherein the first trap and the second trap are configurable to be in gaseous communication through the second valve, wherein the first trap and the fourth valve are configurable to be in gaseous communication through the second valve, wherein second trap is configurable to be in gaseous communication with the third valve, wherein the fourth valve is configurable to be in gaseous communication with at least the third trap, wherein the third trap is configurable to be in gaseous communication with the third valve, wherein the third valve is configurable to be in gaseous communication with at least a second device. Each of the first valve, the second valve, the third valve, and the fourth valve, are independently configurable to change between or among gaseous communication flow paths within the collection system. Each of the first valve, the second valve, the third valve, and the fourth valve, are independently configurable to be in gaseous communication with He flow meters (or the He scrubbing system). Each of the first valve, third valve, and the fourth valve, are independently configurable to be in gaseous communication with outlet vents.

In an aspect, the first device described above and herein comprises: a combustion oven configured to combust a sample to produce a gaseous sample, wherein the gaseous sample comprises one or more of the following: $CO_2$, $NO_x$ (x is 1 to 2), and $SO_2$; a first water trap in gaseous communication with the combustion oven, wherein the first water trap is configured to remove water from the gaseous sample exiting the combustion oven; a gas chromatograph oven and column system in gaseous communication with the first water trap, wherein the gas chromatograph oven and column system comprises at least one gas chromatographic column in an oven; and optionally a second water trap in gaseous communication with the gas chromatograph oven and column system, wherein the second water trap is configured to remove water from the gaseous sample exiting the gas chromatograph oven and column system; wherein a collection system in gaseous communication with the second water trap, wherein the collection system is configured to introduce each of $CO_2$, $N_2$, and $SO_2$ to the second device independently of one another; wherein the second device is an analysis system that is in gaseous communication with the collection system, wherein the analysis system optionally comprises an isotope-ratio mass spectrometer (IRMS).

In another aspect, the present disclosure provides for a method of separating two or more gases comprising: flowing the gaseous sample to a gas chromatograph that is configured to separate $CO_2$ and $NO_x$ (x=1-2) from $SO_2$ to form a $CO_2$ and $NO_x$ gaseous sample by heating the gas chromatograph to about 50 to 75° C.; flowing a gaseous sample comprising $CO_2$ and $NO_x$ through a copper reduction column and converting the $NO_x$ to $N_2$ to form a $CO_2$ and $N_2$ gaseous sample; flowing the $CO_2$ and $N_2$ gaseous sample and trapping the $CO_2$ in a first trap to form a $N_2$ gaseous sample; flowing the $N_2$ gaseous sample and trapping the $N_2$ gaseous sample in a third trap, optionally; releasing the $N_2$ gaseous sample(s) from the third trap and flowing to a second device; releasing the $CO_2$ from the first trap to form a $CO_2$ gaseous sample; flowing the $CO_2$ gaseous sample (optionally in a He carrier gas flow at about 20 to 200 mL/min) and trapping the $CO_2$ gaseous sample in a second trap; releasing the $CO_2$ gaseous sample(s) and flowing to a second device; optionally, increasing the temperature of the gas chromatograph to about 200 to 280° C. to form a $SO_2$ gaseous sample; flowing the $SO_2$ gaseous sample and exposing the $SO_2$ gaseous sample to a water trap to remove or substantially remove water (e.g., from the sample, carrier gas) from the $SO_2$ gaseous sample; flowing the $SO_2$ gaseous sample and trapping the $SO_2$ gaseous sample in the first trap; releasing the $SO_2$ gaseous sample(s) from the first trap; flowing the $SO_2$ gaseous sample and trapping the $SO_2$ gaseous sample in the second trap; and releasing the $SO_2$ gaseous sample(s) and flowing to the second device. The method also includes analyzing one or more of the $N_2$ gaseous sample(s), the $CO_2$ gaseous sample(s), and the $SO_2$ gaseous sample(s), independently of one another, using the second device and wherein the second device is an isotope-ratio mass spectrometer (IRMS).

In another aspect, the present disclosure provides for a collection system comprising: a first valve, a second valve, a third valve, and fourth valve and a first trap, a second trap, and a third trap, wherein the first valve is configurable to be in gaseous communication with at least the second valve and optionally a first device, wherein the second valve is configurable to be in gaseous communication with at least the first trap, the second trap, or the fourth valve, wherein the first trap and the second trap are configurable to be in gaseous communication through the second valve, wherein the first trap and the fourth valve are configurable to be in gaseous communication through the second valve, wherein second trap is configurable to be in gaseous communication with the third valve, wherein the fourth valve is configurable to be in gaseous communication with at least the third trap, wherein the third trap is configurable to be in gaseous communication with the third valve, wherein the third valve is optionally configurable to be in gaseous communication with at least a second device. The system can comprise one, two or all of the following: each of the first valve, the second valve, the third valve, and the fourth valve, are independently configurable to change between or among gaseous communication flow paths within the collection system; each of the first valve, the second valve, the third valve, and the fourth valve, are independently configurable to be in gaseous communication with He flow meters; or each of the first valve, the third valve, and the fourth valve, are independently configurable to be in gaseous communication with outlet vents.

In addition, the system can include one or more of the following: the second trap is a liquid nitrogen trap having a fused silica capillary, wherein the fused silica capillary has a first elevated position that is in a position that is not within liquid nitrogen and a second immersed position that has the fused silica capillary in a position that is within liquid nitrogen; the third trap is a liquid nitrogen trap having a silica gel packed tubing, wherein the silica gel packed tubing has a first elevated position that is in a position that is not within liquid nitrogen and a second immersed position that is in a position that has the silica gel packed tubing within liquid nitrogen; or first trap is a liquid nitrogen trap having a deactivated stainless steel structure, wherein the deactivated stainless steel structure has a first elevated position that is in a position that is not within liquid nitrogen and a second immersed position that is in a position that has the deactivated stainless steel structure within liquid nitrogen. In addition, the He flow meters are in gaseous communication with a He introduction trap system, wherein the He introduction trap system includes at least one liquid nitrogen trap having a fused silica capillary.

In another embodiment, the present disclosure provides for a method of separating two or more gases comprising: flowing the $CO_2$ and $N_2$ gaseous sample and trapping the $CO_2$ in a first trap to form a $N_2$ gaseous sample; flowing the $N_2$ gaseous sample and trapping the $N_2$ gaseous sample in a third trap, optionally, one or more additional $N_2$ gaseous samples are trapped in the third trap with the $N_2$ gaseous sample; releasing the $CO_2$ from the first trap to form a $CO_2$ gaseous sample; flowing the $CO_2$ gaseous sample (optionally in a He carrier gas flow of about 20 to 200 mL/min) and trapping the $CO_2$ gaseous sample in a second trap, optionally, one or more additional $CO_2$ gaseous samples are trapped in the second trap with the $CO_2$ gaseous sample; releasing the $CO_2$ gaseous sample(s) and flowing to a second device; flowing a $SO_2$ gaseous sample (optionally in a He carrier gas flow of about 20 to 200 mL/min) and exposing the $SO_2$ gaseous sample to a water trap to remove or substantially (e.g., 90% or more, 95% or more, 99% or more removed) remove water from the $SO_2$ gaseous sample; flowing the $SO_2$ gaseous sample (optionally in a He carrier gas flow of about 20 to 200 mL/min) and trapping the $SO_2$ gaseous sample in the first trap, optionally, one or more additional $SO_2$ gaseous samples are trapped in the first trap with the $SO_2$ gaseous sample; releasing the $SO_2$ gaseous sample(s) from the first trap; and flowing the $SO_2$ gaseous sample (optionally in a He carrier gas flow of about 20 to 200 mL/min) and trapping the $SO_2$ gaseous sample in the second trap, optionally, one or more additional $SO_2$ gaseous samples are trapped in the second trap with the $SO_2$ gaseous sample.

In yet another aspect, the present disclosure provides for a method of separating two or more gases comprising: flowing a gaseous sample including two or more gases A and B (optionally gas C), and trapping gas A in a first trap to form a gaseous B sample including gas B; flowing the gaseous B sample and trapping the gaseous B sample in a third trap, optionally, one or more additional gaseous B samples are trapped in the third trap with the gaseous B sample; releasing the gaseous B sample(s) and flowing to a second device; releasing gas A from the first trap to form a gaseous A sample; flowing the gaseous A sample and trapping the gaseous A sample in a second trap, optionally, one or more additional gaseous A sample are trapped in the second trap with the gaseous A sample; and releasing the gaseous A sample(s) and flowing to the second device. In addition, the method includes flowing a gaseous C sample including gas C and exposing the gaseous C sample to a water trap to remove or substantially remove water from the gaseous C sample; flowing the gaseous C sample and trapping the gaseous C sample in the first trap, optionally, one or more additional gaseous C samples are trapped in the first trap with the gaseous C sample; releasing the gaseous C sample(s) from the first trap; and flowing the gaseous C sample and trapping the gaseous C sample in the second trap, optionally, one or more additional gaseous C samples are trapped in the second trap with the gaseous C sample.

BRIEF DESCRIPTION OF THE DRAWINGS

Further aspects of the present disclosure will be more readily appreciated upon review of the detailed description of its various embodiments, described below, when taken in conjunction with the accompanying drawings. schematic

DETAILED DESCRIPTION

Figure 1:
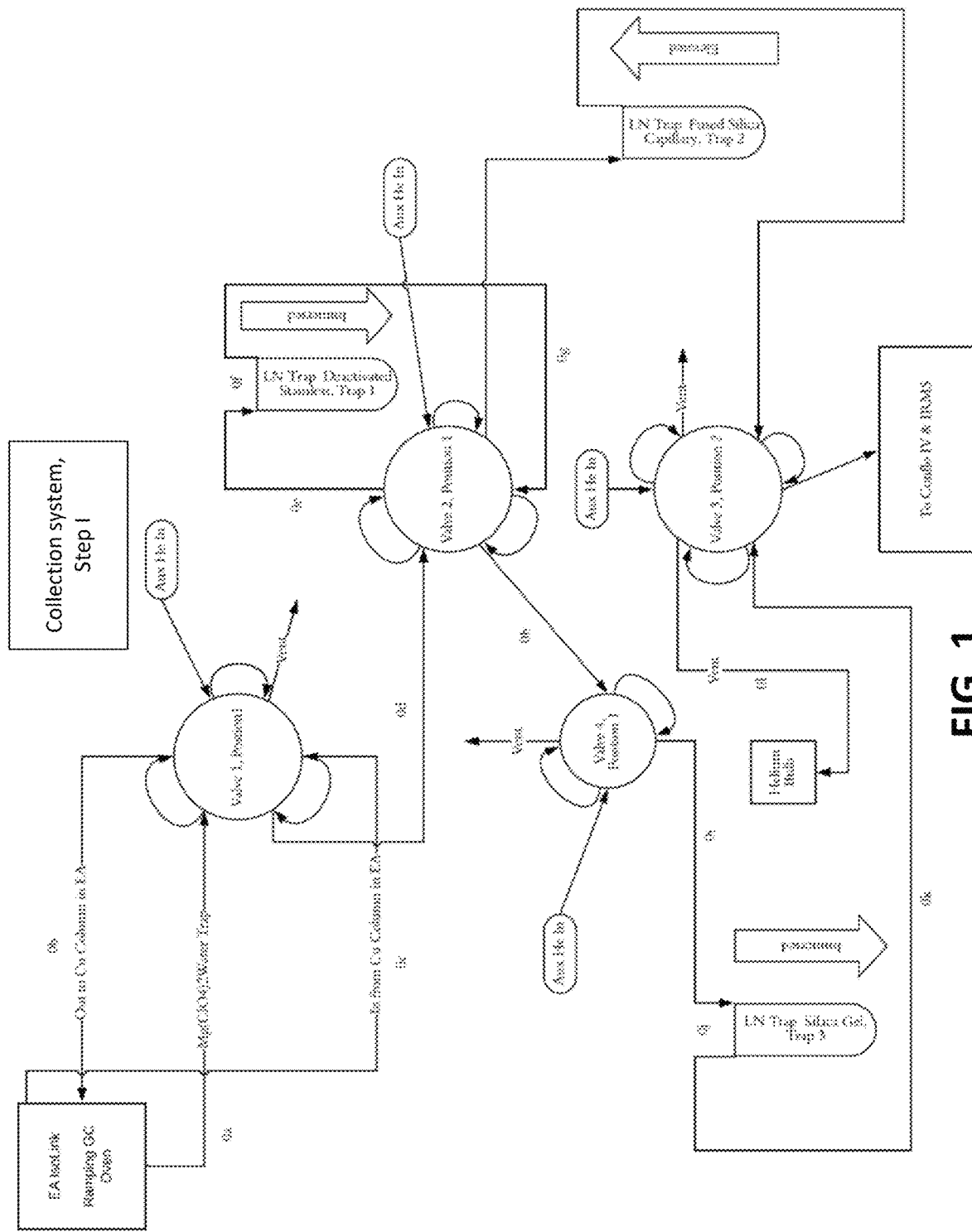
FIGS. 1-6 illustrates schematics and schematic steps I to VI of the use of a system of the present disclosure.

Generally, embodiments of the present disclosure provide for collection and separation systems, collection and separation methods, isotope analysis systems, methods of processing samples to analyze $^{15}N$, $^{13}C$, and $S^{34}$, and the like. The collection and separation systems and collection and separation methods may be referred to as "collection system" and "collection method" for reasons of brevity.

This disclosure is not limited to particular embodiments described, and as such may, of course, vary. The terminology used herein serves the purpose of describing particular embodiments only, and is not intended to be limiting, since the scope of the present disclosure will be limited only by the appended claims.

Where a range of values is provided, each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method may be carried out in the order of events recited or in any other order that is logically possible.

Embodiments of the present disclosure will employ, unless otherwise indicated, techniques of analytical chemistry and the like, which are within the skill of the art. Such techniques are explained fully in the literature.

Prior to describing the various embodiments, the following definitions are provided and should be used unless otherwise indicated.

Unless otherwise defined, all technical and scientific terms used herein have the same meaning as commonly understood by one of ordinary skill in the art of microbiology, molecular biology, medicinal chemistry, and/or organic chemistry. Although methods and materials similar or equivalent to those described herein can be used in the practice or testing of the present disclosure, suitable methods and materials are described herein.

As used in the specification and the appended claims, the singular forms "a," "an," and "the" may include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Discussion:

Embodiments of the present disclosure include systems and methods of collection and separation. The systems and methods can be used to separate one or more gases from a gaseous sample. For example, each of $CO_2$, $N_2$, and $SO_2$ can be separated and flowed to another device (e.g., to determine amounts). Subsequently, the one or more gases (e.g., $CO_2$, $N_2$, and $SO_2$) can be analyzed, for example using an isotope analysis system. The system can include a collection system that is in gaseous communication with a first device (e.g., a chromatographic system), where the collection system can be in gaseous communication with another device at another outlet to analyze the gases, independently of one another. For example, the collection system can be configured to isolate two or more gases of a gaseous sample and configured to introduce each to a second device independently of one another. FIGS. 1-8 illustrate diagrams that describe the system and method of collection and separation within a larger system.

Advantages of embodiments of the present disclosure include the ability to control release of trapped sample gas species for entry into a detection system (e.g., mass spectrometer) in a simple and straightforward manner. Reliance on a GC oven and separatory column, alone, is no longer a requirement as with previous systems. With previous systems, it was necessary to send all sample gas products simultaneously through the mass spectrometer, which is no longer required using embodiments of the present disclosure since it allows venting of $N_2$ and $CO_2$ to atmosphere, if desired, with sole collection of $SO_2$ for $^{34}S$ determination. For samples with sulfur concentrations lower than 0.01%), it is possible using embodiments of the present disclosure to combust several replicates of same sample, venting $N_2$ and $CO_2$ to atmosphere while consecutively collecting $SO_2$ aliquots for release at one time. In addition, lower He carrier gas flows can be used to achieve equal or greater detection limits as previous systems. Also, the He carrier gas flow can be adjusted for either high or low throughput, unlike other systems, which gives the present system versatility of use. In addition, the He carrier gas can be scrubbed so it includes a lower concentration of $N_2$, which otherwise needs to be accounted for. Previous or standard elemental analyzer—isotope ratio mass spectrometer (EA-IRMS) systems were limited to microgram quantities of total element at or near 20 micrograms. Embodiments of the present disclosure have a sensitivity to 100 nanograms total element or lower if employing the "stacking" technique for same sample aliquot additions for concentration of sample gas, which is described in more detail below.

In an aspect, the collection system is configured to isolate each of $CO_2$, $N_2$, and $SO_2$ of a gaseous sample. The collection system is also configured to introduce each of $CO_2$, $N_2$, and $SO_2$ to a second device independently of one another. The second device can be an analysis system that is in gaseous communication with the collection system. The analysis system optionally can comprise an isotope-ratio mass spectrometer (IRMS).

The collection system can include a first valve, a second valve, a third valve, and fourth valve and a first trap, a second trap, and a third trap. The first valve is configurable to be in gaseous communication with at least the second valve and the first device. The second valve is configurable to be in gaseous communication with at least the first trap, the second trap, or the fourth valve. The first trap and the second trap are configurable to be in gaseous communication through the second valve. The first trap and the fourth valve are configurable to be in gaseous communication through the second valve. The second trap is configurable to be in gaseous communication with the third valve. The fourth valve is configurable to be in gaseous communication with at least the third trap. The third trap is configurable to be in gaseous communication with the third valve. The third valve is configurable to be in gaseous communication with at least the second device. The first valve, the second valve, the third valve, and the fourth valve as well as tubing connecting each of these as well as the traps, can be made of a material that is inert, such as stainless steel or the like. The dimensions (e.g., thickness on the range of mm to cm) of the valves and tubes are appropriate to flow the gases.

Each of the first valve, the second valve, the third valve, and the fourth valve, are independently configurable to change between or among gaseous communication flow paths within the collection system.

Figure 8:
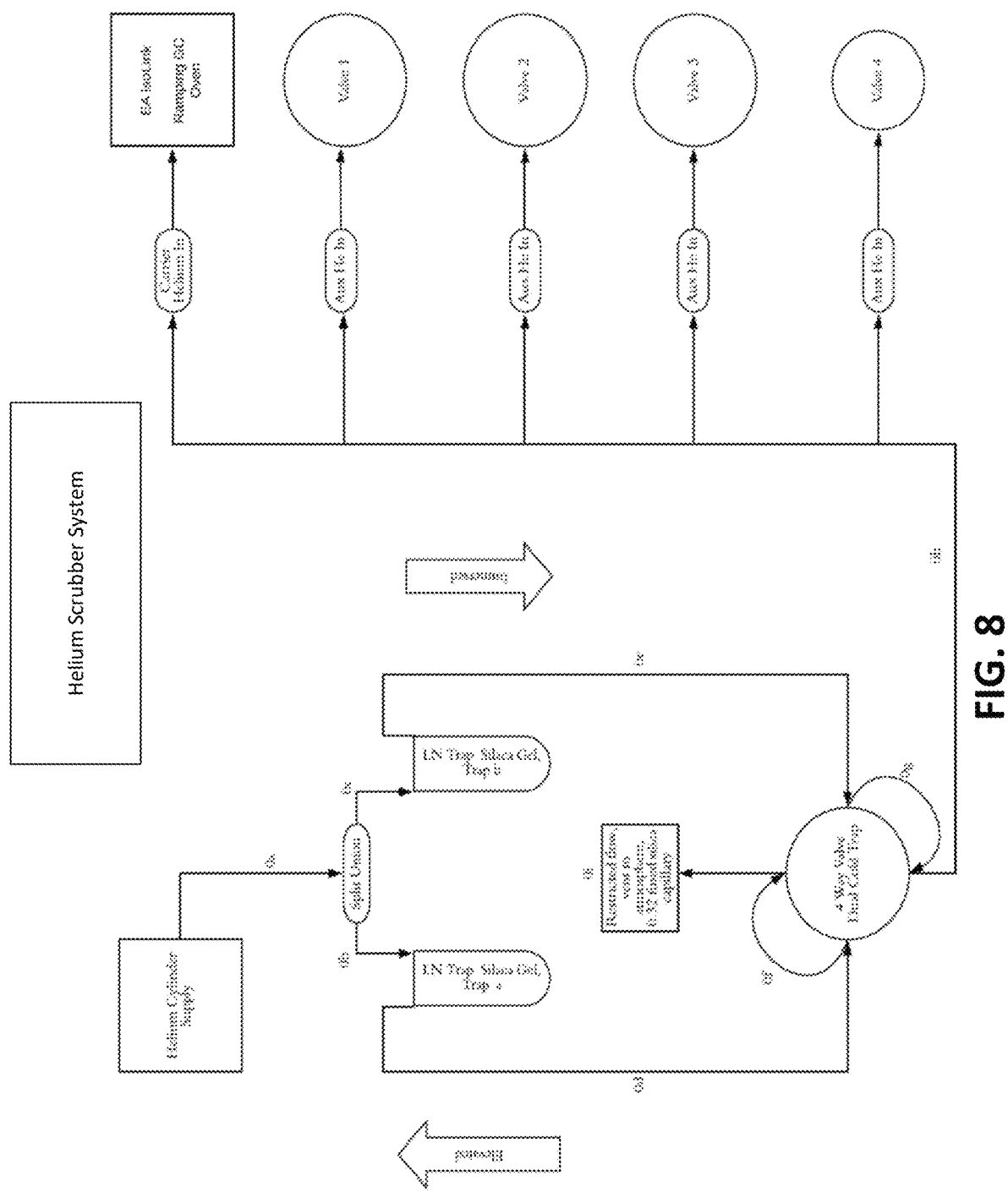
FIG. 8 illustrates a schematic of a helium scrubbing system.

Each of the first valve, the second valve, the third valve, and the fourth valve, are independently configurable to be in gaseous communication with He flow meters, which may be part of or independent from the Helium scrubber system as described in FIG. 8.

Each of the first valve, third valve, and the fourth valve, are independently configurable to be in gaseous communication with outlet vents (e.g. to atmosphere or vacuum).

The second trap is a liquid nitrogen trap having a fused silica capillary. The fused silica capillary has a first elevated position that is in a position that is not within liquid nitrogen and a second immersed position that has the fused silica capillary in a position that is within liquid nitrogen.

The third trap is a liquid nitrogen trap having a silica gel packed tubing. The silica gel packed tubing has a first elevated position that is in a position that is not within liquid nitrogen and a second immersed position that is in a position that has the silica gel packed tubing within liquid nitrogen.

The first trap is a liquid nitrogen trap having a deactivated stainless steel structure. The deactivated stainless steel structure has a first elevated position that is in a position that is not within liquid nitrogen and a second immersed position that is in a position that has the deactivated stainless steel structure within liquid nitrogen.

The first device can include a combustion oven configured to combust a sample to produce a gaseous sample. The gaseous sample can include one or more of the following: $CO_2$, $NO_x$ (x is 1 to 2), and $SO_2$. A first water trap can be in gaseous communication with the combustion oven. The first water trap can be configured to remove water from the gaseous sample exiting the combustion oven. A gas chromatograph oven and the column system can be in gaseous communication with the first water trap. The gas chromatograph oven and column system comprise at least one gas chromatographic column in an oven. A second water trap can be in gaseous communication with the gas chromatograph oven and column system. The second water trap can be configured to remove water from the gaseous sample exiting the gas chromatograph oven and column system. The collection system can be in gaseous communication with the second water trap. The collection system can be configured to introduce each of $CO_2$, $N_2$, and $SO_2$ to the second device independently of one another.

The second device can be an analysis system that is in gaseous communication with the collection system. The analysis system optionally can comprise an isotope-ratio mass spectrometer (IRMS).

In addition, the analysis system can optionally include a He carrier gas scrubber system (also referred to as "He introduction trap system") to remove contaminants from the He flow and interfaced at one or more points in the collection system (See FIGS. 1-8). In reference to "in a He carrier gas flow" as provided herein, the He is flowed through the He introduction trap system" or alternatively if a He introduction trap system is not used, using a traditional He flow system as used in similar systems (e.g., a mass spectrometry system). While He can be obtained having low concentrations of contaminants, $N_2$ is a contaminant that can pose difficulties since $N_2$ is being measured. This can be accommodated, but this is not ideal, so removal of as much $N_2$ as possible is best. In this regard, a He carrier gas scrubber system (such as shown in FIG. 8) can be used to remove $N_2$ or reduce the amounts of $N_2$ to negligible levels (e.g., less than 0.01%). The He introduction trap system uses one or more liquid nitrogen traps packed with a trap material such a silica gel or similar material used in liquid nitrogen traps to remove contaminant such as $N_2$. The He carrier gas can be flowed into the liquid nitrogen trap, where $N_2$ in the He carrier gas is frozen in the trap material. After a period of time or time window, typically a single sample analysis, the He flow can be flowed through a second liquid nitrogen trap while the original liquid nitrogen traps is allowed to vent or is put under a vacuum to remove the contaminants from the trap material before it is used again. In particular, the first or original liquid nitrogen trap can be withdrawn from liquid nitrogen and a vacuum can be applied to remove the $N_2$ and other contaminants present in the trap material as its temperature rises or allowed to vent to atmosphere. In other words, when one liquid nitrogen trap is being used (e.g., He carrier gas is flowed there through), it is submerged in liquid nitrogen, the other liquid nitrogen trap can be under vacuum to remove contaminants. If needed, additional liquid nitrogen traps can be used in this manner. Once the scrubbed He carrier gas passes through the liquid nitrogen trap, the He carrier gas can be routed (e.g., in gaseous communication) to the appropriate areas of the system (e.g., valves 1-4, detectors, and the like).

In an aspect, the He carrier gas scrubber system can include two liquid nitrogen traps, where a first liquid nitrogen trap is immersed in liquid nitrogen for the duration of an analytical acquisition "window" for a single sample. Then first liquid nitrogen trap is raised at the end of a given acquisition window and optionally after all sample peaks for $N_2$, $CO_2$ and $SO_2$ have eluted. A connecting valve such as shown in FIG. 8, between the two liquid nitrogen traps and the incoming He supply can be switched to allow trapped contaminant $N_2$ to elute to vent/atmosphere/vacuum and at the same time lowering the second trap. The vent outlet of He scrubber valve outflow is limited as to not waste helium unnecessarily via a flow limiting length (≥30.5 cm long, 0.32 mm i.d.) of fused silica capillary. The second valve position can send incoming He through the second liquid nitrogen trap immersed in liquid nitrogen. In an aspect, each liquid nitrogen trap is immersed in liquid nitrogen only for a period of time equal to or less than entire, single sample acquisition and greater than the retention time of the last eluting sample peak.

In an aspect, the method of separating two or more gases can include: optionally, flowing the gaseous sample (optionally in a He carrier gas flow of is about 160 to 200 mL/min) to a gas chromatograph that is configured to separate $CO_2$ and $NO_x$ from $SO_2$ to form a $CO_2$ and $NO_x$ gaseous sample by heating the gas chromatograph to about 50 to 75° C.; optionally, flowing a gaseous sample comprising (or consisting of) $CO_2$ and $NO_x$ (optionally in a He carrier gas flow of is about 20 to 200 mL/min) through a copper reduction column and converting the $NO_x$ to $N_2$ to form a $CO_2$ and $N_2$ gaseous sample; flowing the $CO_2$ and $N_2$ gaseous sample and trapping the $CO_2$ in a first trap to form a $N_2$ gaseous sample; flowing the $N_2$ gaseous sample and trapping the $N_2$ gaseous sample in a third trap, optionally, one or more additional $N_2$ gaseous samples are trapped in the third trap with the $N_2$ gaseous sample; optionally, releasing the $N_2$ gaseous sample(s) from the third trap and flowing to a second device; releasing the $CO_2$ from the first trap to form a $CO_2$ gaseous sample; flowing the $CO_2$ gaseous sample (optionally in a He carrier gas flow of is about 20 to 200 mL/min) and trapping the $CO_2$ gaseous sample in a second trap, optionally, one or more additional $CO_2$ gaseous samples are trapped in the second trap with the $CO_2$ gaseous sample; optionally, releasing the $CO_2$ gaseous sample(s) and flowing to a second device; optionally, increasing the temperature of the gas chromatograph to about 200 to 280° C. to form a $SO_2$ gaseous sample; flowing the $SO_2$ gaseous sample (optionally in a He carrier gas flow of is about 20 to 200 mL/min) and exposing the $SO_2$ gaseous sample to a water trap to remove or substantially remove water from the $SO_2$ gaseous sample; flowing the $SO_2$ gaseous sample (optionally in a He carrier gas flow of is about 20 to 200 mL/min) and trapping the $SO_2$ gaseous sample in the first trap, optionally, one or more additional $SO_2$ gaseous samples are trapped in the first trap with the $SO_2$ gaseous sample; releasing the $SO_2$ gaseous sample(s) from the first trap; flowing the $SO_2$ gaseous sample (optionally in a He carrier gas flow of is about 20 to 200 mL/min) and trapping the $SO_2$ gaseous sample in the second trap, optionally, one or more additional $SO_2$ gaseous samples are trapped in the second trap with the $SO_2$ gaseous sample; and optionally, releasing the $SO_2$ gaseous sample(s) (optionally in a He flow is about 20 to 200 mL/min) and flowing to the second device.

The method can also include analyzing each of the $N_2$ gaseous sample(s), $CO_2$ gaseous sample(s), and $SO_2$ gaseous sample(s), independently of each other, using the second device and wherein the second device is optionally an isotope-ratio mass spectrometer (IRMS).

The method can be implemented using any one of the systems provided herein. In this regard, the method can include: flowing the $CO_2$ and $NO_x$ gaseous sample through the copper reduction column and converting the $NO_x$ to $N_2$ to form the $CO_2$ and $N_2$ gaseous sample further comprises configuring the second valve to flow the $CO_2$ and $N_2$ gaseous sample to the first trap; flowing the $N_2$ gaseous sample and trapping the $N_2$ gaseous sample further comprises configuring the second valve to flow the $N_2$ gaseous sample to the fourth valve, wherein the fourth valve is configured to flow the $N_2$ gaseous sample to the third trap; and releasing the $N_2$ gaseous sample(s) from the third trap further comprises configuring the third valve to flow the $N_2$ gaseous sample to the second device.

In addition, the method can include: releasing the $CO_2$ from the first trap to form the $CO_2$ gaseous sample further comprises configuring the second valve to flow the $CO_2$ gaseous sample to the second trap; and releasing the $CO_2$ gaseous sample(s) comprises configuring the third valve to flow the $CO_2$ gaseous sample to the second device.

In addition, the method can include: flowing the $SO_2$ gaseous sample and trapping the $SO_2$ gaseous sample in the first trap, further comprises configuring the second valve to flow the $SO_2$ gaseous sample to the first trap; flowing the $SO_2$ gaseous sample and trapping the $SO_2$ gaseous sample in the second trap, further comprises configuring the second valve to flow the $SO_2$ gaseous sample to the second trap; and releasing the $SO_2$ gaseous sample(s) and analyzing the $SO_2$ gaseous sample(s) using the isotope-ratio mass spectrometer (IRMS), further comprises configuring the third valve to flow the $SO_2$ gaseous sample to the analysis system.

In another aspect, the method of separating two or more gases can include: flowing the $CO_2$ and $N_2$ gaseous sample and trapping the $CO_2$ in a first trap to form a $N_2$ gaseous sample; flowing the $N_2$ gaseous sample and trapping the $N_2$ gaseous sample in a third trap, optionally, one or more additional $N_2$ gaseous samples (different runs or replicates from the same sample, which can "stack" the samples to provide more accurate, precise, and/or superior detection limits) are trapped in the third trap with the $N_2$ gaseous sample; releasing the $CO_2$ from the first trap to form a $CO_2$ gaseous sample; flowing the $CO_2$ gaseous sample (optionally in a He carrier gas flow of is about 20 to 200 mL/min) and trapping the $CO_2$ gaseous sample in a second trap, optionally, one or more additional $CO_2$ gaseous samples (stacking) are trapped in the second trap with the $CO_2$ gaseous sample; releasing the $CO_2$ gaseous sample(s) and flowing to a second device; flowing a $SO_2$ gaseous sample (optionally in a He carrier gas flow of is about 20 to 200 mL/min) and exposing the $SO_2$ gaseous sample to a water trap to remove or substantially remove water from the $SO_2$ gaseous sample; flowing the $SO_2$ gaseous sample (optionally in a He carrier gas flow of is about 20 to 200 mL/min) and trapping the $SO_2$ gaseous sample in the first trap, optionally, one or more additional $SO_2$ gaseous samples (stacking) are trapped in the first trap with the $SO_2$ gaseous sample; releasing the $SO_2$ gaseous sample(s) from the first trap; and flowing the $SO_2$ gaseous sample (optionally in a He carrier gas flow of is about 20 to 200 mL/min) and trapping the $SO_2$ gaseous sample in the second trap, optionally, one or more additional $SO_2$ gaseous samples are trapped in the second trap with the $SO_2$ gaseous sample.

The method can be implemented using any system provided herein. In this regard, the method includes: flowing the $N_2$ gaseous sample and trapping the $N_2$ gaseous sample further comprises configuring the second valve to flow the $N_2$ gaseous sample to the fourth valve, wherein the fourth valve is configured to flow the $N_2$ gaseous sample to the third trap. In addition, the method includes: releasing the $CO_2$ from the first trap to form the $CO_2$ gaseous sample further comprises configuring the second valve to flow the $CO_2$ gaseous sample to the second trap. The method also includes: flowing the $SO_2$ gaseous sample and trapping the $SO_2$ gaseous sample in the first trap, further comprises configuring the second valve to flow the $SO_2$ gaseous sample to the first trap; and flowing the $SO_2$ gaseous sample and trapping the $SO_2$ gaseous sample in the second trap, further comprises configuring the second valve to flow the $SO_2$ gaseous sample to the second trap.

Optionally, the He carrier gas can be scrubbed as described in relation to He carrier gas scrubber system (also see FIG. 8) to remove contaminants. The method can be used in any system provided herein. In this regard, the method includes: flowing the He carrier gas and trapping the contaminants (e.g., $N_2$, water, etc.) into one or one or more liquid nitrogen traps. The He carrier gas that emerges is scrubbed and flowed to one or more of the valves (e.g., first-fourth), the detector, or other component described herein. If needed, the flow of the He carrier gas can be flowed into another liquid nitrogen trap if the original liquid nitrogen trap needs to be evacuated. Additional details are provided herein and in view of FIG. 8 and the associated discussion.

The present disclosure also provides for isotope analysis systems, methods of processing samples to analyze $^{15}N$, $^{13}C$, and $S^{34}$, and the like enable the analysis of $^{15}N$, $^{13}C$, and $S^{34}$ in samples that overcome deficiencies of current technologies. FIGS. 1-8 include diagrams that describe the isotope analysis system and methods of processing samples to analyze $^{15}N$, $^{13}C$, and $S^{34}$. In addition, FIGS. 1-8 provide steps on how the isotope analysis system would process the collection, separation, and stacking of $CO_2$, $N_2$, and $SO_2$ so that each can be separately analyzed using an analysis system such as isotope-ratio mass spectrometer (IRMS) to measure $^{15}N$, $^{13}C$, and/or $S^{34}$ of a sample. Separation and collection of the analysis of each of $CO_2$, $N_2$, and $SO_2$ results in more accurate and precise measurements of the amount $^{15}N$, $^{13}C$, and/or $S^{34}$ of present in a sample. Unlike other systems, if the amount of any one of $CO_2$, $N_2$, and $SO_2$ is relatively low, one or more replicates can be processed so that the $CO_2$, $N_2$, and $SO_2$ can be "stacked" (e.g., the amount in each replicate can be added together and then analyzed as one), which allows much lower detection limits (e.g., nanogram level (e.g., about 100 nanograms) as compared to 20 micrograms of current systems).

Also, the isotope analysis system and methods of processing samples can adjust the flow of He across a broad range (e.g., about 10 ml/min to 200 ml/min) depending upon the demands of the user (e.g., quick analysis to save time, slower analysis to save He, and the like) and provide equally good results across that range unlike other systems. Furthermore, problems associated with water in the system (e.g., the water reacts with $SO_2$ to produce sulfuric acid within the system that can result in damage to the system) can be eliminated or significantly reduced (e.g., greater than 80%, 90%, 95%, or 99%) relative to other systems. Additional advantages or features of the isotope analysis system and methods of processing samples are provided in FIGS. 1-8.

Now having described embodiments of the present disclosure, additional features and combinations are described below. In addition, the following description can be understood in view of FIGS. 1-8 and their associated discussion.

In an aspect, the system, includes a collection system in gaseous communication with a first device, wherein the collection system is configured to isolate two or more gases of a gaseous sample and configured to introduce each to a second device independently of one another.

The system as described herein, wherein the collection system is configured to isolate one or more of $CO_2$, $N_2$, and $SO_2$ (optionally two or more or optionally each of $CO_2$, $N_2$, and $SO_2$) of a gaseous sample and configured to introduce each of $CO_2$, $N_2$, and $SO_2$ to a second device independently of one another.

The system as described herein, wherein the collection system comprises a first valve, a second valve, a third valve, and fourth valve and a first trap, a second trap, and a third trap, wherein the first valve is configurable to be in gaseous communication with at least the second valve and the first device, wherein the second valve is configurable to be in gaseous communication with at least the first trap, the second trap, or the fourth valve, wherein the first trap and the second trap are configurable to be in gaseous communication through the second valve, wherein the first trap and the fourth valve are configurable to be in gaseous communication through the second valve, wherein second trap is configurable to be in gaseous communication with the third valve, wherein the fourth valve is configurable to be in gaseous communication with at least the third trap, wherein the third trap is configurable to be in gaseous communication with the third valve, wherein the third valve is configurable to be in gaseous communication with at least the second device.

The system as described herein, wherein each of the first valve, the second valve, the third valve, and the fourth valve, are independently configurable to change between or among gaseous communication flow paths within the collection system.

The system as described herein, wherein each of the first valve, the second valve, the third valve, and the fourth valve, are independently configurable to be in gaseous communication with He flow meters.

The system as described herein, wherein each of the first valve, third valve, and the fourth valve, are independently configurable to be in gaseous communication with outlet vents.

The system as described herein, wherein the second trap is a liquid nitrogen trap having a fused silica capillary, wherein the fused silica capillary has a first elevated position that is in a position that is not within liquid nitrogen and a second immersed position that has the fused silica capillary in a position that is within liquid nitrogen.

The system as described herein, wherein the third trap is a liquid nitrogen trap having a silica gel packed tubing, wherein the silica gel packed tubing has a first elevated position that is in a position that is not within liquid nitrogen and a second immersed position that is in a position that has the silica gel packed tubing within liquid nitrogen.

The system as described herein, wherein the first trap is a liquid nitrogen trap having a deactivated stainless steel structure, wherein the deactivated stainless steel structure has a first elevated position that is in a position that is not within liquid nitrogen and a second immersed position that is in a position that has the deactivated stainless steel structure within liquid nitrogen.

The system as described herein, wherein the first device comprises: a combustion oven configured to combust a sample to produce a gaseous sample, wherein the gaseous sample comprises one or more of the following: $CO_2$, $NO_x$ (x is 1 to 2), and $SO_2$; a first water trap in gaseous communication with the combustion oven, wherein the first water trap is configured to remove water from the gaseous sample exiting the combustion oven; a gas chromatograph oven and column system in gaseous communication with the first water trap, wherein the gas chromatograph oven and column system comprises at least one gas chromatographic column in an oven; and a second water trap in gaseous communication with the gas chromatograph oven and column system, wherein the second water trap is configured to remove water from the gaseous sample exiting the gas chromatograph oven and column system; wherein the collection system in gaseous communication with the second water trap, wherein the collection system is configured to introduce each of $CO_2$, $N_2$, and $SO_2$ to the second device independently of one another; wherein the second device is an analysis system that is in gaseous communication with the collection system, wherein the analysis system optionally comprises an isotope-ratio mass spectrometer (IRMS).

The system as described herein, further comprises a He introduction trap system, wherein the He introduction trap system includes at least one liquid nitrogen trap having a fused silica capillary, wherein the liquid nitrogen trap has a first elevated position that is in a position that is not within liquid nitrogen and a second immersed position that has the liquid nitrogen trap in a position that is within liquid nitrogen.

The system as described herein, wherein the He introduction trap system includes a first liquid nitrogen trap and a second liquid nitrogen trap, wherein the first liquid nitrogen trap and the liquid nitrogen trap are positioned in parallel with another.

In an aspect, the system of separating two or more gases includes: optionally, flowing the gaseous sample (optionally in a He carrier gas flow of is about 160 to 200 mL/min) to a gas chromatograph that is configured to separate $CO_2$ and $NO_x$ from $SO_2$ to form a $CO_2$ and $NO_x$ gaseous sample by heating the gas chromatograph to about 50 to 75° C.; optionally, flowing a gaseous sample comprising (or consisting of) $CO_2$ and $NO_x$ (optionally in a He carrier gas flow of is about 20 to 200 mL/min) through a copper reduction column and converting the $NO_x$ to $N_2$ to form a $CO_2$ and $N_2$ gaseous sample; flowing the $CO_2$ and $N_2$ gaseous sample and trapping the $CO_2$ in a first trap to form a $N_2$ gaseous sample; flowing the $N_2$ gaseous sample and trapping the $N_2$ gaseous sample in a third trap, optionally, one or more additional $N_2$ gaseous samples are trapped in the third trap with the $N_2$ gaseous sample; optionally, releasing the $N_2$ gaseous sample(s) from the third trap and flowing to a second device; releasing the $CO_2$ from the first trap to form a $CO_2$ gaseous sample; flowing the $CO_2$ gaseous sample (optionally in a He carrier gas flow of is about 20 to 200 mL/min) and trapping the $CO_2$ gaseous sample in a second trap, optionally, one or more additional $CO_2$ gaseous samples are trapped in the second trap with the $CO_2$ gaseous sample; optionally, releasing the $CO_2$ gaseous sample(s) and flowing to a second device; optionally, increasing the temperature of the gas chromatograph to about 200 to 280° C. to form a $SO_2$ gaseous sample; flowing the $SO_2$ gaseous sample (optionally in a He carrier gas flow of is about 20 to 200 mL/min) and exposing the $SO_2$ gaseous sample to a water trap to remove or substantially remove water from the $SO_2$ gaseous sample; flowing the $SO_2$ gaseous sample (optionally in a He carrier gas flow of is about 20 to 200 mL/min) and trapping the $SO_2$ gaseous sample in the first trap, optionally, one or more additional $SO_2$ gaseous samples are trapped in the first trap with the $SO_2$ gaseous sample; releasing the $SO_2$ gaseous sample(s) from the first trap; flowing the $SO_2$ gaseous sample (optionally in a He carrier gas flow of is about 20 to 200 mL/min) and trapping the $SO_2$ gaseous sample in the second trap, optionally, one or more additional $SO_2$ gaseous samples are trapped in the second trap with the $SO_2$ gaseous sample; and optionally, releasing the $SO_2$ gaseous sample(s) (optionally in a He carrier gas flow of is about 20 to 200 mL/min) and flowing to the second device.

The method as described herein, further comprises analyzing the $N_2$ gaseous sample(s) using the second device and wherein the second device is optionally an isotope-ratio mass spectrometer (IRMS).

The method as described herein, further comprises analyzing the $CO_2$ gaseous sample(s) using the second device and wherein the second device is optionally an isotope-ratio mass spectrometer (IRMS).

The method as described herein, further comprises analyzing the $SO_2$ gaseous sample(s) using the second device and wherein the second device is optionally an isotope-ratio mass spectrometer (IRMS).

The method as described herein, further comprises the system of as described above or herein and wherein: flowing the $CO_2$ and $NO_x$ gaseous sample through the copper reduction column and converting the $NO_x$ to $N_2$ to form the $CO_2$ and $N_2$ gaseous sample further comprises configuring the second valve to flow the $CO_2$ and $N_2$ gaseous sample to the first trap; flowing the $N_2$ gaseous sample and trapping the $N_2$ gaseous sample further comprises configuring the second valve to flow the $N_2$ gaseous sample to the fourth valve, wherein the fourth valve is configured to flow the $N_2$ gaseous sample to the third trap; and releasing the $N_2$ gaseous sample(s) from the third trap further comprises configuring the third valve to flow the $N_2$ gaseous sample to the second device.

The method as described herein, wherein: releasing the $CO_2$ from the first trap to form the $CO_2$ gaseous sample further comprises configuring the second valve to flow the $CO_2$ gaseous sample to the second trap; releasing the $CO_2$ gaseous sample(s) comprises configuring the third valve to flow the $CO_2$ gaseous sample to the second device.

The method as described herein, wherein: flowing the $SO_2$ gaseous sample and trapping the $SO_2$ gaseous sample in the first trap, further comprises configuring the second valve to flow the $SO_2$ gaseous sample to the first trap; flowing the $SO_2$ gaseous sample and trapping the $SO_2$ gaseous sample in the second trap, further comprises configuring the second valve to flow the $SO_2$ gaseous sample to the second trap; and releasing the $SO_2$ gaseous sample(s) and analyzing the $SO_2$ gaseous sample(s) using the isotope-ratio mass spectrometer (IRMS), further comprises configuring the third valve to flow the $SO_2$ gaseous sample to the analysis system.

The method as described herein, he steps of the method can be implemented using the system described above and herein.

The method as described herein, further comprises flow any one of the gaseous sample using a purified He flow, wherein the purified He flow is obtained by flowing a regular He through a He introduction trap system, wherein the one or more contaminants are removed from the regular He to produce purified He.

In an aspect, the collection system includes: a first valve, a second valve, a third valve, and fourth valve and a first trap, a second trap, and a third trap, wherein the first valve is configurable to be in gaseous communication with at least the second valve and optionally a first device, wherein the second valve is configurable to be in gaseous communication with at least the first trap, the second trap, or the fourth valve, wherein the first trap and the second trap are configurable to be in gaseous communication through the second valve, wherein the first trap and the fourth valve are configurable to be in gaseous communication through the second valve, wherein second trap is configurable to be in gaseous communication with the third valve, wherein the fourth valve is configurable to be in gaseous communication with at least the third trap, wherein the third trap is configurable to be in gaseous communication with the third valve, wherein the third valve is optionally configurable to be in gaseous communication with at least a second device.

In some embodiments of the system described herein, each of the first valve, the second valve, the third valve, and the fourth valve, are independently configurable to change between or among gaseous communication flow paths within the collection system.

In some embodiments of the system described herein, each of the first valve, the second valve, the third valve, and the fourth valve, are independently configurable to be in gaseous communication with He flow meters.

In some embodiments of the system described herein, each of the first valve, third valve, and the fourth valve, are independently configurable to be in gaseous communication with outlet vents.

In some embodiments of the system described herein, the second trap is a liquid nitrogen trap having a fused silica capillary, wherein the fused silica capillary has a first elevated position that is in a position that is not within liquid nitrogen and a second immersed position that has the fused silica capillary in a position that is within liquid nitrogen.

In some embodiments of the system described herein, the third trap is a liquid nitrogen trap having a silica gel packed tubing, wherein the silica gel packed tubing has a first elevated position that is in a position that is not within liquid nitrogen and a second immersed position that is in a position that has the silica gel packed tubing within liquid nitrogen.

In some embodiments of the system described herein, the first trap is a liquid nitrogen trap having a deactivated stainless steel structure, wherein the deactivated stainless steel structure has a first elevated position that is in a position that is not within liquid nitrogen and a second immersed position that is in a position that has the deactivated stainless steel structure within liquid nitrogen.

In some embodiments of the system described herein, the He flow meters are in gaseous communication with a He introduction trap system, wherein the He introduction trap system includes at least one liquid nitrogen trap having a fused silica capillary, wherein the liquid nitrogen trap has a first elevated position that is in a position that is not within liquid nitrogen and a second immersed position that has the liquid nitrogen trap in a position that is within liquid nitrogen.

In some embodiments of the system described herein, the He introduction trap system includes a first liquid nitrogen trap and a second liquid nitrogen trap, wherein the first liquid nitrogen trap and the liquid nitrogen trap are positioned in parallel with another.

In an aspect, the method of separating two or more gases includes: flowing the $CO_2$ and $N_2$ gaseous sample and trapping the $CO_2$ in a first trap to form a $N_2$ gaseous sample; flowing the $N_2$ gaseous sample and trapping the $N_2$ gaseous sample in a third trap, optionally, one or more additional $N_2$ gaseous samples are trapped in the third trap with the $N_2$ gaseous sample; releasing the $CO_2$ from the first trap to form a $CO_2$ gaseous sample; flowing the $CO_2$ gaseous sample (optionally in a He carrier gas flow of is about 20 to 200 mL/min) and trapping the $CO_2$ gaseous sample in a second trap, optionally, one or more additional $CO_2$ gaseous samples are trapped in the second trap with the $CO_2$ gaseous sample; releasing the $CO_2$ gaseous sample(s) and flowing to a second device; flowing a $SO_2$ gaseous sample (optionally in a He carrier gas flow of is about 20 to 200 mL/min) and exposing the $SO_2$ gaseous sample to a water trap to remove or substantially remove water from the $SO_2$ gaseous sample; flowing the $SO_2$ gaseous sample (optionally in a He carrier gas flow of is about 20 to 200 mL/min) and trapping the $SO_2$ gaseous sample in the first trap, optionally, one or more additional $SO_2$ gaseous samples are trapped in the first trap with the $SO_2$ gaseous sample; releasing the $SO_2$ gaseous sample(s) from the first trap; and flowing the $SO_2$ gaseous sample (optionally in a He carrier gas flow of is about 20 to 200 mL/min) and trapping the $SO_2$ gaseous sample in the second trap, optionally, one or more additional $SO_2$ gaseous samples are trapped in the second trap with the $SO_2$ gaseous sample.

The method can further comprise the system as described above and wherein: flowing the $N_2$ gaseous sample and trapping the $N_2$ gaseous sample further comprises configuring the second valve to flow the $N_2$ gaseous sample to the fourth valve, wherein the fourth valve is configured to flow the $N_2$ gaseous sample to the third trap.

In some embodiments the method as described herein can include: releasing the $CO_2$ from the first trap to form the $CO_2$ gaseous sample further comprises configuring the second valve to flow the $CO_2$ gaseous sample to the second trap.

In some embodiments the method as described herein can include: flowing the $SO_2$ gaseous sample and trapping the $SO_2$ gaseous sample in the first trap, further comprises configuring the second valve to flow the $SO_2$ gaseous sample to the first trap; and flowing the $SO_2$ gaseous sample and trapping the $SO_2$ gaseous sample in the second trap, further comprises configuring the second valve to flow the $SO_2$ gaseous sample to the second trap.

In some embodiments the method as described herein can include steps implemented using the system as described above and provided herein.

In an aspect, the method of separating two or more gases includes: flowing a gaseous sample including two or more gases and trapping gas A in a first trap to form a gaseous B sample including gas B; flowing the gaseous B sample and trapping the gaseous B sample in a third trap, optionally, one or more additional gaseous B samples are trapped in the third trap with the gaseous B sample; releasing the gaseous B sample(s) and flowing to a second device; releasing gas A from the first trap to form a gaseous A sample; flowing the gaseous A sample (optionally in a He carrier gas flow of is about 20 to 200 mL/min) and trapping the gaseous A sample in a second trap, optionally, one or more additional gaseous A sample are trapped in the second trap with the gaseous A sample; and releasing the gaseous A sample(s) and flowing to the second device.

The method as described herein can include, flowing a gaseous C sample including gas C (optionally in a He carrier gas flow of is about 20 to 200 mL/min) and exposing the gaseous C sample to a water trap to remove or substantially remove water from the gaseous C sample; flowing the gaseous C sample (optionally in a He carrier gas flow of is about 20 to 200 mL/min) and trapping the gaseous C sample in the first trap, optionally, one or more additional gaseous C samples are trapped in the first trap with the gaseous C sample; releasing the gaseous C sample(s) from the first trap; and flowing the gaseous C sample (optionally in a He carrier gas flow of is about 20 to 200 mL/min) and trapping the gaseous C sample in the second trap, optionally, one or more additional gaseous C samples are trapped in the second trap with the gaseous C sample.

The method as described herein can be implemented using the system as described above and herein.

In regard to FIGS. 1-8, the following provides a step by step description of FIGS. 1-8.

Device Flow Path, Step 1, FIG. 1:

Ia Combustion effluent gas (excess $O_2$, $NO_x$ (x=1-2) and $CO_2$) is routed out of EA Isolink through magnesium perchlorate water trap to Valve I, in position 1. (The EA Isolink is a ThermoFisher manufactured elemental combustion analyzer device. N.B. EA=elemental analyzer. This system is where solid samples are loaded into carousel trays for timed drop into a combustion column for oxidation/conversion into $NO_x$, $CO_2$ and $SO_2$. The model type is the "Isolink" which means this model has unique design features as compared to previous models (e.g. EA Flash 2000). The EA Isolink system is the first to employ both a helium management system (not used in methods or systems described herein) and the outboard, ramping GC oven.)

Ib Combustion effluent gas (excess $O_2$, $NO_x$ and $CO_2$) is routed through Valve 1, in load position, and back out to EA Isolink copper reduction column to allow capture of excess $O_2$ and reduction of $NO_x$ to $N_2$.

Ic $N_2$ and $CO_2$ gases sent back to Valve 1.

Id $N_2$ and $CO_2$ gases routed out of Valve 1 and to Valve 2, both in position 1.

Ie $N_2$ and $CO_2$ gases routed out of Valve 1 to Trap 1, LN cryo-trap, deactivated stainless steel where $CO_2$ gas is trapped/frozen. $N_2$ is not trapped and allowed to pass unaffected.

If LN (liquid nitrogen) Trap (Trap 1) Deactivated Stainless tubing immersed in Dewar of liquid nitrogen (1/16" o.d., 1.0 mm i.d., 0.5 m length).

Ig $N_2$ sample gas moves forward while $CO_2$ gas remains trapped (e.g., frozen) in Trap 1.

Ih is $N_2$ sample gas routed out of Valve 2 and forward to Valve 4, in position 1.

Ii $N_2$ sample gas routed from Valve 4 to LN Trap (Trap 3).

Ij LN Trap (Trap 3) SilcoSmooth tubing packed with silica gel grade 12, 35/60 mesh (1/16" o.d., 1.0 mm i.d., 0.5 m length). LN Trap 3 is immersed in liquid nitrogen for this Load 1 step.

Ik in this "load" step, only helium carrier gas is routed out of Trap 3, with $N_2$ sample gas effectively trapped in Trap 3, immersed in liquid nitrogen. Helium carrier gas is routed from Trap 3 to Valve 3.

Il Helium carrier gas effluent from Trap 3 is routed out of vent capillary (0.32 mm fused silica capillary 12" long) at Valve 3, in position 2. The vent capillary should either be of sufficient length and/or be routed into an inverted glass bulb of sufficient volume to prevent pulling atmosphere into LN Silica. Gel Trap 3. In an aspect, this can be accomplished by using a rigidly mounted 14 mL exetainer as a helium reservoir or bulb with the open end pointing downward. The 0.32 fused silica capillary (12" long) is routed up and into this helium reservoir so that the end of capillary is located withing 10 mm of the closed end of the exetainer.

Figure 2:
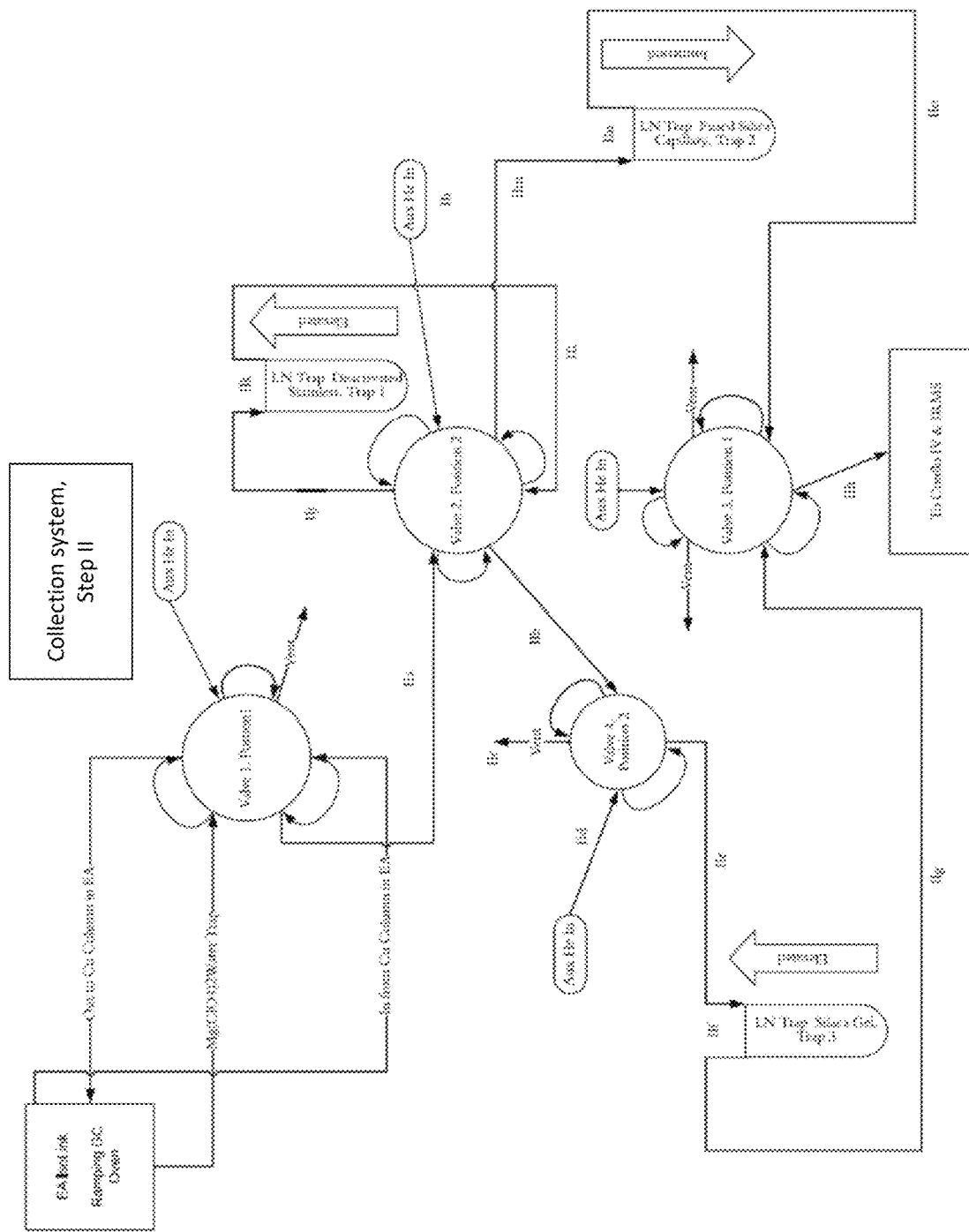

Device Flow Path, Step II, FIG. 2:

N.B. Carrier flow paths for Valve 1 are unchanged in Step if so no descriptions are included in Step II.

IIa Helium carrier gas flow switched in Valve 2 to second position. Incoming line from Valve 1 is routed to Valve 2.

IIb Valve 4 switched to second position. Carrier gas effluent from Valve 2 is routed to Valve 4.

IIc Carrier gas vented to atmosphere.

IId Auxiliary Helium (lower static flow) line into Valve 4.

IIe Helium carrier gas routed to Trap 3.

IIf Trap 3 elevated at same time as Trap 1 and not less than 60 seconds after Valve 2 and Valve 4 are switched to second position.

IIg Carrier gas effluent from Trap 3 with $N_2$ sample gas, after elevation of Trap 3, routed to Valve 3.

IIh Carrier gas effluent out of Valve 3 and routed to Conflo IV for measurement of $N_2$ sample gas. (The Conflo IV is made by Thermo Fisher Scientific and is an interface device that allows sample gas in a helium carrier stream to be introduced to the isotope ratio mass spectrometer. The term, in mass spectrometry language, is called an "open split" which means excess sample gas is vented to atmosphere while a controlled amount is carried to the inlet of the mass spectrometer source via a fused silica capillary. The limitation or need of the IRMS source is for ~10 mL/min of helium carrier flow to reach the open split. The typical helium carrier flow coming from the elemental analyzer is at least 100 mL/min and a PRE split has to be mounted at the rear of the Conflo to effectively route 90% of the carrier helium and sample gas to atmosphere. This provides the 10 mL/min of required helium flow to then be routed internally to the open split, housed within the Conflo IV interface. The design of methods and systems of the present disclosure, for the first time, provides a static helium flow from my auxiliary helium, of ~10 ml/min to the IRMS interface, Methods and systems of the present disclosure take the necessary higher flow from the elemental analyzer (EA IsoLink) and deposits sample gas aliquots in each of the traps then allows the much lower, static helium flow from my auxiliary helium supply to then push the sample gas aliquots into the Conflo IV interface and open split, Essentially, no sample gas or carrier gas is now required to vent prior to presentation to open split and IRMS inlet. Again, the limitation or requirement of the isotope ratio mass spectrometer of 10 mL/min of helium carrier gas being met without the need for venting any carrier gas, with sample aliquots, to atmosphere.

IIi Auxiliary helium carrier gas (lower static flow) routed into Valve 2, in second position.

IIj Helium carrier flow routed out of Valve 2 and into Trap 1.

IIk Trap 1 elevated at same time as Trap 3 and not less than 60 seconds after Valve 2 and Valve 4 are switched to second position, as described in "IIf".

IIl Helium carrier effluent from Trap 1 routed back to Valve 2 and out to Trap 2, now with $CO_2$ sample gas post elevation of Trap 1.

IIm Helium carrier effluent from Valve 2 routed to Trap 2.

IIn Trap 2 is immersed in LN not less than 30 seconds before elevating Traps 1 and 3. Trap 2 is a 5 meter length of 0.32 mm i.d. fused silica capillary held in place, during operation, by a special bracket. $CO_2$ released from Trap 1 is captured by smaller internal diameter and immersed Trap 2 allowing for much improved chromatography during subsequent elevation and release into helium carrier stream.

IIo Helium carrier gas (lower static flow) allowed to flow to Valve 3 and vented to atmosphere.

Figure 3:
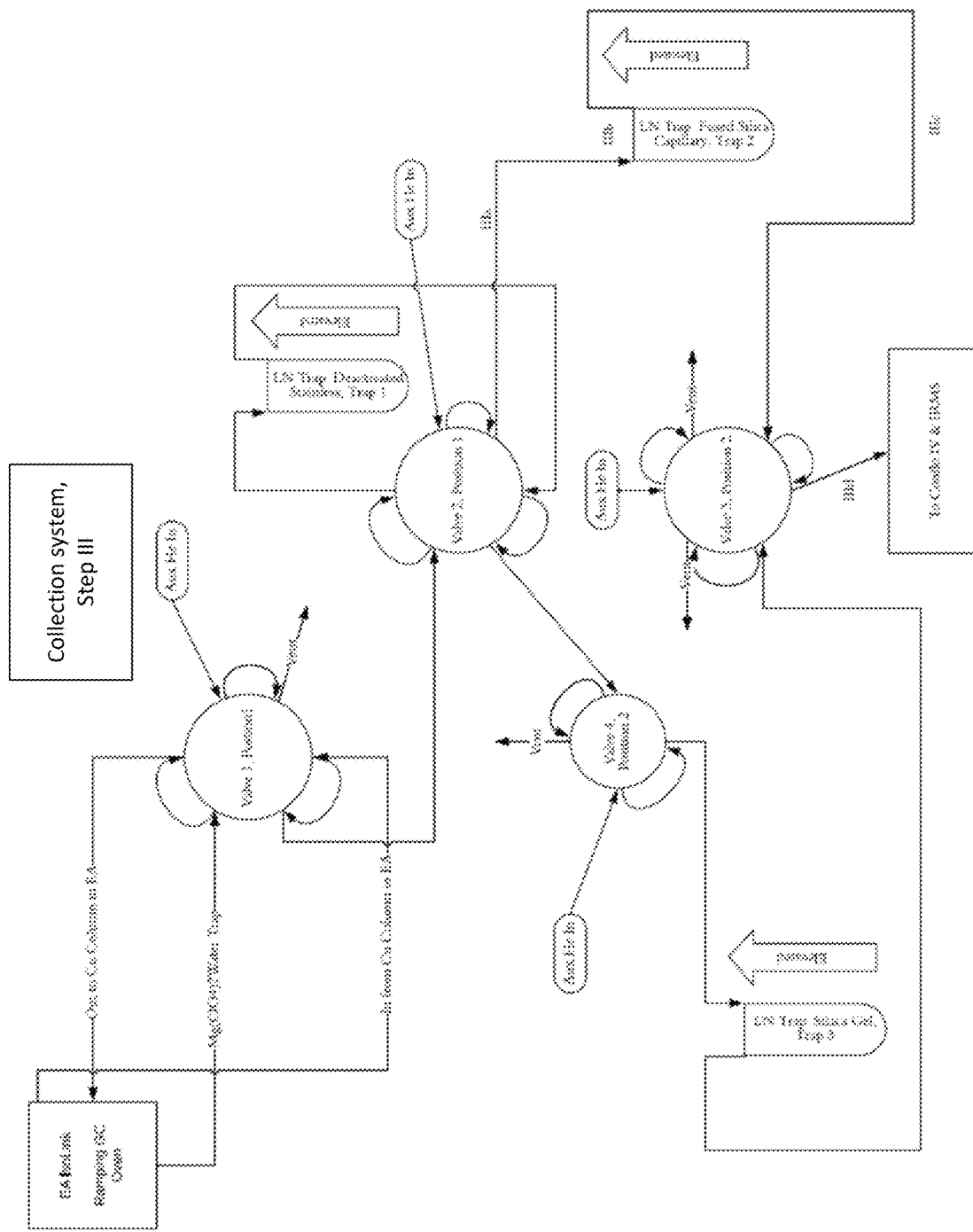

Device Flow Path, Step III, FIG. 3:

IIIa Auxiliary helium carrier gas routed through Valve 2, switched to position 1 and out to Trap 2.

IIIb Trap 2 is elevated not less than 90 seconds after switching Valve 2 to position 1.

IIIc Trapped $CO_2$ is allowed to sublimate and gas is routed to Valve 3, in position IIId $CO_2$ sample gas is carried via auxiliary helium carrier stream into Conflo IV and IRMS for detection.

Figure 4:
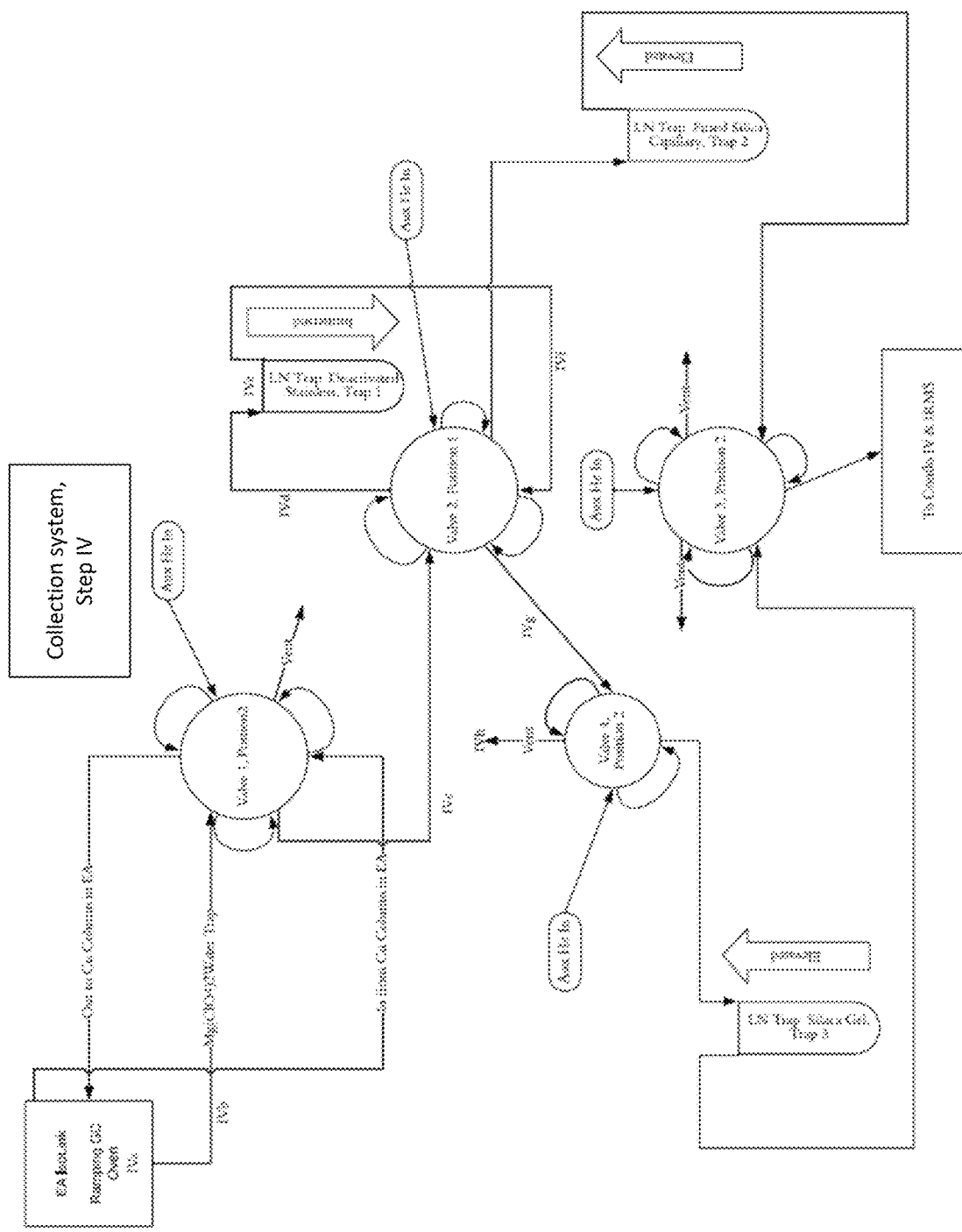

Device Flow Path, Step IV, FIG. 4:

Step IV is initiated during event occurring in section IIf. After a period of time of at least 60 seconds, after procedure described in section IIf, Trap 1 is once again immersed into the liquid nitrogen container.

IVa EA IsoLink, outboard ramping SC oven heating protocol initiated. Temperature of separatory GC column is taken from 70° C. to 240° C. to allow release of $SO_2$.

IVb Released $SO_2$ is routed out of SC oven and directly into a magnesium perchlorate water trap. A water trap or any chemical column downstream of a SC separation column is usually harmful to chromatography, peak separation, shape, etc. Here, using the present system, this helps in the determination of $SO_2$ and $^{34}S$ due to our observation that $H_2O$ is also released from SC column as it passes the 100° C. mark. These observations have shown a marked improvement in both chromatography and long-term precision. Allowing collected moisture to travel downstream and into capillaries prior to the elution of $SO_2$ gave erratic results for our measurements. The ability of $SO_2$ to readily absorb into any water lining downstream capillaries manifested itself as lower and lower measured $^{34}S$ values, owing to possible fractionation at the interactive surfaces of captured moisture. Lower and lower $_{34}S$ values were inevitably followed by extremely high $^{34}S$ values (×10 per mil) which would be explained by the uncontrolled release of the fractionated, heavier isotope at the same interactive surfaces of captured moisture. The addition of a magnesium perchlorate water trap immediately downstream of the EA IsoLink's ramping SC oven attempts to completely eliminate downstream moisture-related fractionation problems. However, it was later learned that the release of $H_2O$ was a problem after the addition of the present system and moisture (as mass 18) was able to be isolated, collected and measured for each individual sample. Even with a magnesium perchlorate water trap immediately downstream of the site of sample combustion, it is evident that some moisture is, in fact, making its way past that first trap and to the separatory SC column along with the other sample gases of interest.

IVc With Valve 1 already set to position 2, the gas effluent from ramped SC column is routed directly to Valve 2, set to position 1.

IVd $SO_2$ gas effluent is routed out of Valve 2, set to position 1 and along to Trap 1, immersed in liquid nitrogen.

IVf $SO_2$ gas, in helium carrier stream is collected in Trap 1, immersed in liquid nitrogen and helium effluent is free to continue back to Valve 2, still in position 1.

IVg Helium carrier effluent from Valve 2 is routed to Valve 4, in position 2 and allowed to vent without hindrance or flow restriction.

IVh Helium carrier vents out of 0.32 mm i.d. capillary, approximately 8" long. This design allows collection of $SO_2$ gas within Trap 1 without any flow restrictions downstream.

Figure 5:
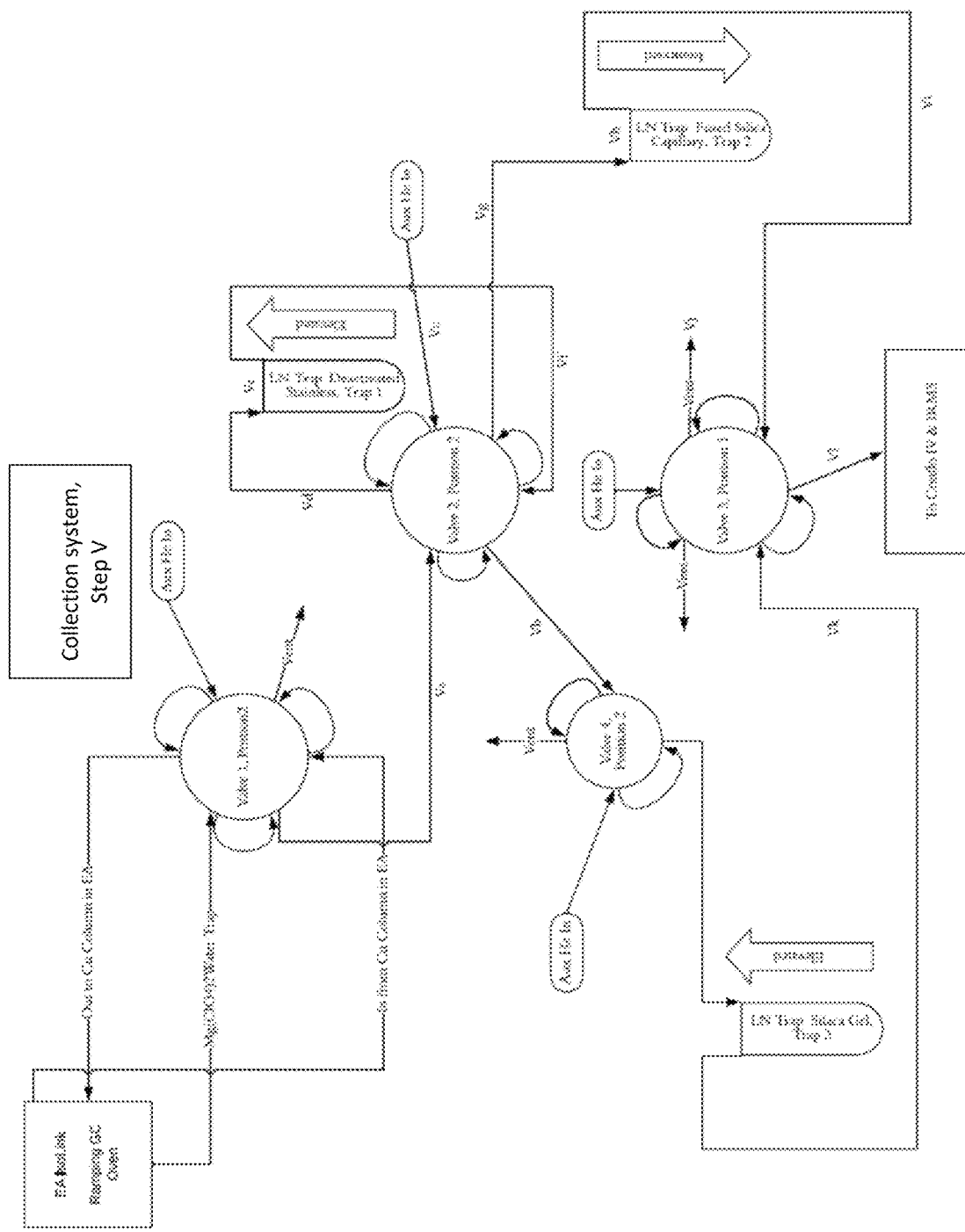

Device Flow Path, Step V, FIG. 5:

Va Valve 2, switched to position 2, and helium carrier gas from Valve 1 now routed to Valve 4.

Vb Helium carrier gas routed to Valve 4 and vented to atmosphere.

Vc Auxiliary helium carrier (reduced static flow) gas now routed to Trap 1.

Vd Auxiliary helium carrier gas out of Valve 2, in position 2, and into Trap 1.

Ve Trap 1 remains immersed in liquid nitrogen dewar vessel for a period of time not less than 30 seconds after switching Valve 1 to position 2. After a period of time not less than 30 seconds after switching Valve 1 to position 2, Trap 1 is elevated out of the liquid nitrogen dewar vessel.

Vf With Trap 1 elevated, cold trapped $SO_2$ is allowed to sublimate and gas effluent carried out of Trap 1 and back to Valve 2 in position 2.

Vg $SO_2$ sample gas routed out of Trap 1 and out to Trap 2 in immersed position.

Vh Trap 2 in immersed position traps $SO_2$ sample gas a second time. Trap 2, with smaller internal diameter, fused silica capillary tubing allows for much better, sharper, taller sample gas peaks when measured at RMS.

Vi,j Helium carrier stream emerges from Valve 3, in position 1, in an uninterrupted fashion and is allowed to vent to atmosphere. The uninterrupted flow of helium carrier stream out of Valve 3, in position 1, provides best possible conditions for deposition of $SO_2$ sample gas on interior walls of capillary tubing in Trap 2.

Vk,l Auxiliary helium flow from Valve 4, in position 2, provides carrier flow (static lower flow) into Valve 3 and forward to MMS system. The continuity of helium flow into IRMS system is critical for preventing any atmospheric gas intrusion.

Figure 6:
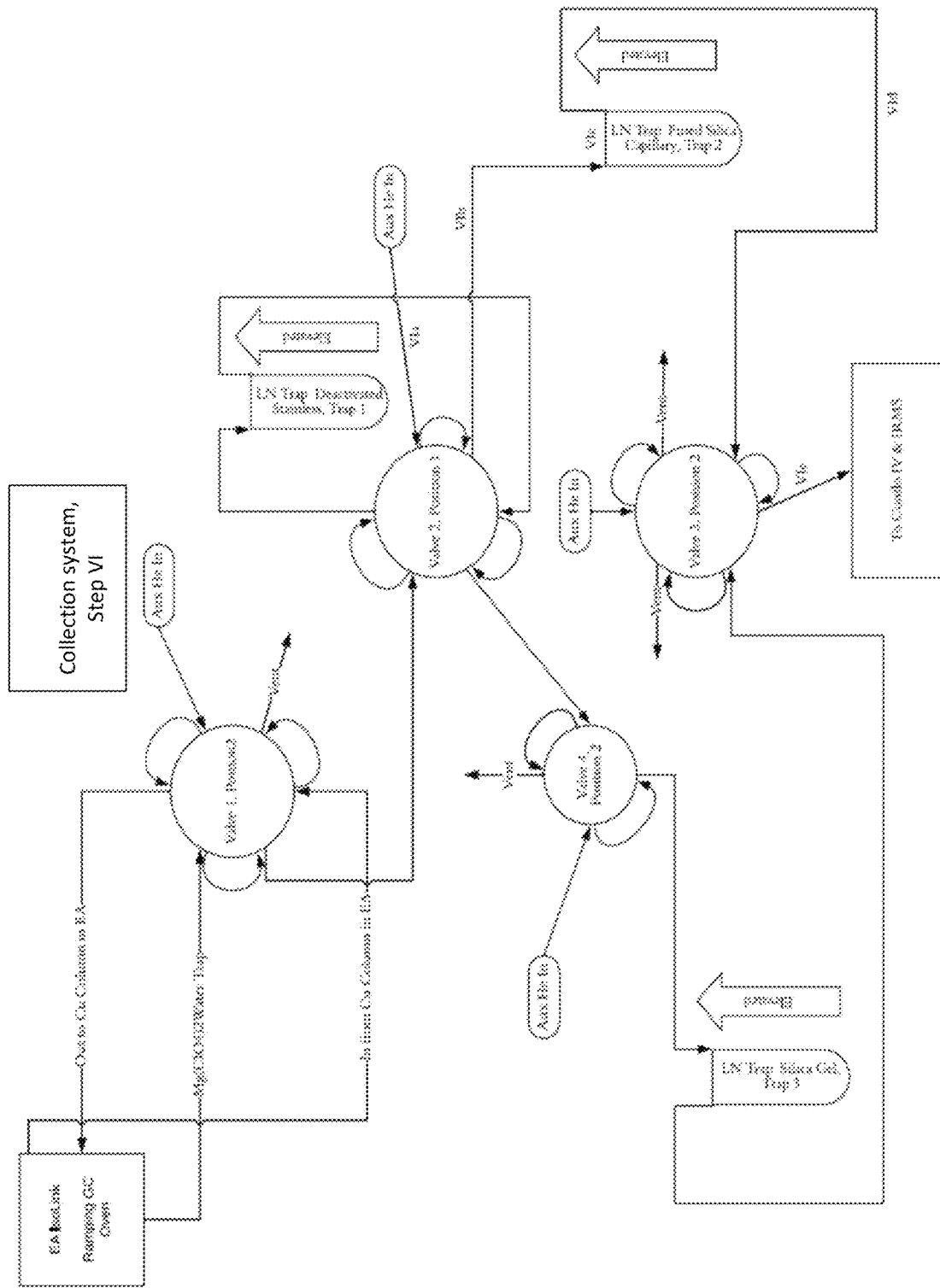

Device Flow Path, Step VI, FIG. 6

VIa Valve 2 is switched back to position 1 after a period of not less than 30 seconds to allow complete evacuation of $SO_2$ sample gas from Trap 1 to Trap 2. Auxiliary helium carrier gas is routed, with Valve 2 in position 1, to Trap 2.

VIb Auxiliary helium carrier flow from Valve 2 is routed to Trap 2, still immersed in liquid nitrogen dewar vessel.

VIc After a period of not less than 30 seconds after switching Valve 2 to position 1, Trap 2 is elevated out of liquid nitrogen dewar vessel, allowing $SO_2$ sample gas to sublimate.

VId $SO_2$ sample gas effluent carried to Valve 3 in position 2.

VIe Concentrated $SO_2$ sample gas effluent routed through and out of Valve 3, in position 2, to IRMS.

Figure 7:
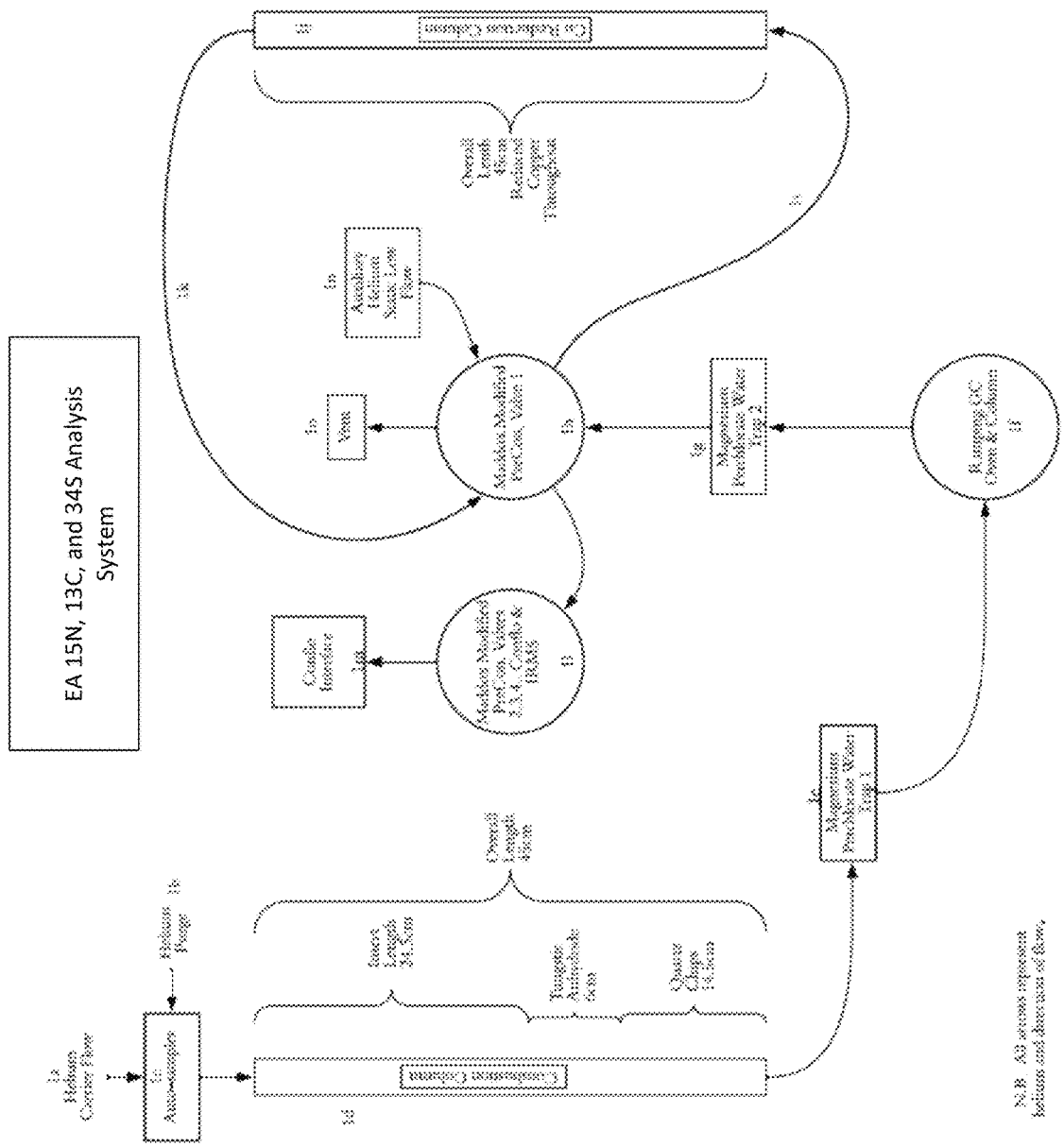
FIG. 7 illustrates a schematic of an elemental analysis system.

EA $^{15}N$, $^{13}C$ & $^{34}S$ Analysis System and Flow Path, FIG. 7:

1a,b,c: Auto-sampler function with the helium purge being supplied by a sole source. This was initiated to minimize problems associated with any potential leaks or flow irregularities with the HeM or manual needle valve system. The HeM valve and needle valve system is completely bypassed with our experimental design. We do, however, use the variable flow control of helium carrier gas provided by the Isodat software and mass flow controller valves within the system.

1d: Unique to this design, our combustion column uses only tungstic anhydride and quart chips. i.e. No reduced copper is used in our combustion column packing design.

1e: While other EA systems have placed a water trap immediately downstream of a combustion column, ours places the water trap extremely close to outlet. In an effort to remove any water, created through combustion of sample material, as quickly as possible from the helium carrier stream, we place our magnesium water trap within 3 cm of the outlet of our combustion column.

1f: Ramping (GC Oven and separatory column functions identically to that described previously (Steps: IVa and IVb)

1g: Unique to the this design, our GC Oven and separatory column out-flow is routed immediately to a second magnesium perchlorate water trap. N.B. Our experiments showed moisture ($H_2O$) contamination of carrier gas lines downstream of GC Oven. Placement of a second magnesium perchlorate water trap immediately downstream of the GC Oven completely removes moisture contamination for helium carrier flow and sample gases into the Condo interface and IRMS. It should also be noted that we observed odd fractionation of $^{34}S$ values prior to the addition of secondary magnesium water trap. Efforts to resolve that fractionation resulted in the determination that moisture, downstream of (GC Oven, was the culprit. As the GC Oven temperature is ramped past 100° C., en route to 240° C., any moisture present in separatory column packing is turned to vapor and carried downstream. Again, the addition of a secondary water trap completely solved the problem.

1h: Unique to this design, the addition of a modified collection system, provides better control or manipulation of sample gases in a number of ways. First, $NO_x$, excess $O_2$ and $CO_2$, eluting from GC separatory column, are routed back to a full-size copper reduction column from collection system Valve 1.

1i Helium carrier and sample gas routed to system on board reduction oven and copper column.

1j A full-size copper reduction column, in a dedicated reduction column oven, may be held at an ideal temperature for reduction of $NO_x$ and removal of excess $O_2$. Typical temperatures for standard elemental analyzer system copper reduction column ovens range from 650 to 750° C. These temperatures are low enough to prevent sintering of the copper wires but high enough to allow best chemical reaction for removing oxygen and reduction of $NO_x$ species. It should be stated that "one column" approach, using combustion catalyst and copper wires in one quartz tube, relies on most of the copper being located just outside the most extreme temperatures of the combustion column oven. In practice, copper wires sinter almost immediately and both reactive surfaces as well as reduction capacity are diminished greatly.

1k $N_2$ and $CO_2$ sample gas effluent is routed from copper reduction column in EA-IsoLink back to Valve 1.

1l Detailed description of exactly how $N_2$, $CO_2$ and $SO_2$ sample gases are separated, concentrated and presented to the mass spectrometer via the collection system are given in separate documents.

1m Unique to the methods and systems provided herein, the elimination of the sample pre-split (10:1 or greater) into Conflo interface is completely eliminated. The much lower, static helium flow provided by helium regulator on board the collection system allows for direct connection to Conflo with entirety of sample gas effluent. Routing entirety of sample and carrier gas flow results in vastly greater sample concentration to mass spectrometer for detection.

1n Auxiliary helium flow to provide lower, static flow for collection system.

1o Vent to allow release to atmosphere of either unwanted/unnecessary sample gases or during direct routing of $SO_2$ away from copper reduction column and to Trap 1. Helium Scrubber Flow Path (an optional element in the systems and methods) (FIG. 8)(it should be state that where it is stated "in a He carrier gas flow", the He gas is provided by the Helium scrubber flow system as described in FIG. 8):

0a: Helium cylinder supply (single cylinder) is split via listed split union into two paths.

0b: Helium is routed to Trap "a". Trap "a" is elevated away from liquid nitrogen in Helium Scrubber figure.

0c: Helium is routed to Trap "b". Trap "b" is immersed in liquid nitrogen in Helium Scrubber figure.

0d: Outflow of elevated Trap "a" is routed to Dual Cold Trap Valco, 4-way valve.

0e: Outflow of immersed Trap "b" is routed to Dual Cold Trap Valco, 4-way valve.

0f: In Dual Cold Trap Valco, 4-way valve position (shown in figure), elevated Trap "a" helium effluent gas is carried to a restricted flow, vent to atmosphere (noted as 0i in figure). The vent, as illustrated, is a 0.32 mm fused silica capillary, 30.5 cm in length.

0g: In Dual Cold Trap Valco, 4-way valve position (shown in figure), immersed Trap "b" helium effluent gas is carried to inlet helium ports in the elemental analyzer as well as distributed to the collection system auxiliary ports. Distribution plumbing manifold is illustrated in figure as Oh.

0i: Restricted, vent to atmosphere, 0.32 mm fused silica capillary, 30.5 cm in length. It should be stated that Helium specifications for UHP Grade helium list measured background $N_2$ values of not more than 5 ppm. Helium specifications for Research Grade helium list measured background $N_2$ values of not more than 0.5 ppm. In either case, it is advantageous to "scrub" helium carrier gas prior to delivery of all analytical components of both the elemental analyzer and the collection system.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

I claim:

1. A system, comprising:
a collection system in gaseous communication with a first device, wherein the collection system is configured to isolate two or more gases of a gaseous sample and configured to introduce each to a second device independently of one another,
wherein the collection system comprises a first valve, a second valve, a third valve, and fourth valve and a first trap, a second trap, and a third trap, wherein the first valve is configurable to be in gaseous communication with at least the second valve and the first device, wherein the second valve is configurable to be in gaseous communication with at least the first trap, the second trap, or the fourth valve, wherein the first trap and the second trap are configurable to be in gaseous communication through the second valve, wherein the first trap and the fourth valve are configurable to be in gaseous communication through the second valve, wherein second trap is configurable to be in gaseous communication with the third valve, wherein the fourth valve is configurable to be in gaseous communication with at least the third trap, wherein the third trap is configurable to be in gaseous communication with the third valve, wherein the third valve is configurable to be in gaseous communication with at least the second device,
wherein each of the first valve, the second valve, the third valve, and the fourth valve, are independently configurable to be in gaseous communication with He flow meters.

2. The system of claim 1, comprising:
wherein the collection system is configured to isolate one or more of $CO_2$, $N_2$, and $SO_2$ of a gaseous sample and configured to introduce each of $CO_2$, $N_2$, and $SO_2$ to a second device independently of one another.

3. A system, comprising:
a collection system in gaseous communication with a first device, wherein the collection system is configured to isolate two or more gases of a gaseous sample and configured to introduce each to a second device independently of one another,
wherein the collection system comprises a first valve, a second valve, a third valve, and fourth valve and a first trap, a second trap, and a third trap, wherein the first valve is configurable to be in gaseous communication with at least the second valve and the first device, wherein the second valve is configurable to be in gaseous communication with at least the first trap, the second trap, or the fourth valve, wherein the first trap and the second trap are configurable to be in gaseous communication through the second valve, wherein the first trap and the fourth valve are configurable to be in gaseous communication through the second valve, wherein second trap is configurable to be in gaseous communication with the third valve, wherein the fourth valve is configurable to be in gaseous communication with at least the third trap, wherein the third trap is configurable to be in gaseous communication with the third valve, wherein the third valve is configurable to be in gaseous communication with at least the second device,
wherein each of the first valve, third valve, and the fourth valve, are independently configurable to be in gaseous communication with outlet vents.

4. The system of claim 1, wherein each of the first valve, the second valve, the third valve, and the fourth valve, are independently configurable to change between or among gaseous communication flow paths within the collection system.

5. The system of claim 1, wherein each of the first valve, the second valve, the third valve, and the fourth valve, are independently configurable to be in gaseous communication with He flow meters.

6. The system of claim 1, wherein each of the first valve, third valve, and the fourth valve, are independently configurable to be in gaseous communication with outlet vents.

7. A system, comprising:
a collection system in gaseous communication with a first device, wherein the collection system is configured to isolate two or more gases of a gaseous sample and configured to introduce each to a second device independently of one another,
wherein the collection system comprises a first valve, a second valve, a third valve, and fourth valve and a first trap, a second trap, and a third trap, wherein the first valve is configurable to be in gaseous communication with at least the second valve and the first device, wherein the second valve is configurable to be in gaseous communication with at least the first trap, the second trap, or the fourth valve, wherein the first trap and the second trap are configurable to be in gaseous communication through the second valve, wherein the first trap and the fourth valve are configurable to be in gaseous communication through the second valve, wherein second trap is configurable to be in gaseous communication with the third valve, wherein the fourth valve is configurable to be in gaseous communication with at least the third trap, wherein the third trap is configurable to be in gaseous communication with the third valve, wherein the third valve is configurable to be in gaseous communication with at least the second device,
wherein the first device comprises:
a combustion oven configured to combust a sample to produce a gaseous sample, wherein the gaseous sample comprises one or more of the following: $CO_2$, $NO_x$ (x is 1 to 2), and $SO_2$;
a first water trap in gaseous communication with the combustion oven, wherein the first water trap is configured to remove water from the gaseous sample exiting the combustion oven;
a gas chromatograph oven and column system in gaseous communication with the first water trap, wherein the gas chromatograph oven and column system comprises at least one gas chromatographic column in an oven; and
a second water trap in gaseous communication with the gas chromatograph oven and column system, wherein the second water trap is configured to remove water from the gaseous sample exiting the gas chromatograph oven and column system;
wherein the collection system in gaseous communication with the second water trap, wherein the collection system is configured to introduce each of $CO_2$, $N_2$, and $SO_2$ to the second device independently of one another;
wherein the second device is an analysis system that is in gaseous communication with the collection system, wherein the analysis system optionally comprises an isotope-ratio mass spectrometer (IRMS).

8. A collection system comprising:
a first valve, a second valve, a third valve, and fourth valve and a first trap, a second trap, and a third trap, wherein the first valve is configurable to be in gaseous communication with at least the second valve and optionally a first device, wherein the second valve is configurable to be in gaseous communication with at least the first trap, the second trap, or the fourth valve, wherein the first trap and the second trap are configurable to be in gaseous communication through the second valve, wherein the first trap and the fourth valve are configurable to be in gaseous communication through the second valve, wherein second trap is configurable to be in gaseous communication with the third valve, wherein the fourth valve is configurable to be in gaseous communication with at least the third trap, wherein the third trap is configurable to be in gaseous communication with the third valve, wherein the third valve is optionally configurable to be in gaseous communication with at least a second device,
wherein each of the first valve, the second valve, the third valve, and the fourth valve, are independently configurable to change between or among gaseous communication flow paths within the collection system; or
wherein each of the first valve, the second valve, the third valve, and the fourth valve, are independently configurable to be in gaseous communication with He flow meters; or wherein each of the first valve, third valve, and the fourth valve, are independently configurable to be in gaseous communication with outlet vents; or
a combination thereof.

9. The system of claim 8, wherein the second trap is a liquid nitrogen trap having a fused silica capillary, wherein the fused silica capillary has a first elevated position that is in a position that is not within liquid nitrogen and a second immersed position that has the fused silica capillary in a position that is within liquid nitrogen.

10. The system of claim 8, wherein the third trap is a liquid nitrogen trap having a silica gel packed tubing, wherein the silica gel packed tubing has a first elevated position that is in a position that is not within liquid nitrogen and a second immersed position that is in a position that has the silica gel packed tubing within liquid nitrogen.

11. The system of claim 8, wherein the first trap is a liquid nitrogen trap having a deactivated stainless steel structure, wherein the deactivated stainless steel structure has a first elevated position that is in a position that is not within liquid nitrogen and a second immersed position that is in a position that has the deactivated stainless steel structure within liquid nitrogen.

12. The system of claim 8, wherein the He flow meters are in gaseous communication with a He introduction trap system, wherein the He introduction trap system includes at least one liquid nitrogen trap having a fused silica capillary.

13. The system of claim 1, wherein the first device comprises:
a combustion oven configured to combust a sample to produce a gaseous sample, wherein the gaseous sample comprises one or more of the following: $CO_2$, $NO_x$ (x is 1 to 2), and $SO_2$;
a first water trap in gaseous communication with the combustion oven, wherein the first water trap is configured to remove water from the gaseous sample exiting the combustion oven;
a gas chromatograph oven and column system in gaseous communication with the first water trap, wherein the gas chromatograph oven and column system comprises at least one gas chromatographic column in an oven; and
a second water trap in gaseous communication with the gas chromatograph oven and column system, wherein the second water trap is configured to remove water from the gaseous sample exiting the gas chromatograph oven and column system;

wherein the collection system in gaseous communication with the second water trap, wherein the collection system is configured to introduce each of $CO_2$, $N_2$, and $SO_2$ to the second device independently of one another;

wherein the second device is an analysis system that is in gaseous communication with the collection system, wherein the analysis system comprises an isotope-ratio mass spectrometer (IRMS).

14. The system of claim 3, comprising:

wherein the collection system is configured to isolate one or more of $CO_2$, $N_2$, and $SO_2$ of a gaseous sample and configured to introduce each of $CO_2$, $N_2$, and $SO_2$ to a second device independently of one another.

15. The system of claim 3, wherein each of the first valve, the second valve, the third valve, and the fourth valve, are independently configurable to change between or among gaseous communication flow paths within the collection system.

16. The system of claim 3, wherein each of the first valve, the second valve, the third valve, and the fourth valve, are independently configurable to be in gaseous communication with He flow meters.

17. The system of claim 3, wherein each of the first valve, third valve, and the fourth valve, are independently configurable to be in gaseous communication with outlet vents.

18. The system of claim 3, wherein the first device comprises:

a combustion oven configured to combust a sample to produce a gaseous sample, wherein the gaseous sample comprises one or more of the following: $CO_2$, $NO_x$ (x is 1 to 2), and $SO_2$;

a first water trap in gaseous communication with the combustion oven, wherein the first water trap is configured to remove water from the gaseous sample exiting the combustion oven;

a gas chromatograph oven and column system in gaseous communication with the first water trap, wherein the gas chromatograph oven and column system comprises at least one gas chromatographic column in an oven; and a second water trap in gaseous communication with the gas chromatograph oven and column system, wherein the second water trap is configured to remove water from the gaseous sample exiting the gas chromatograph oven and column system;

wherein the collection system in gaseous communication with the second water trap, wherein the collection system is configured to introduce each of $CO_2$, $N_2$, and $SO_2$ to the second device independently of one another;

wherein the second device is an analysis system that is in gaseous communication with the collection system, wherein the analysis system comprises an isotope-ratio mass spectrometer (IRMS).

19. The system of claim 7, comprising:

wherein the collection system is configured to isolate one or more of $CO_2$, $N_2$, and $SO_2$ of a gaseous sample and configured to introduce each of $CO_2$, $N_2$, and $SO_2$ to a second device independently of one another.

20. The system of claim 7, wherein each of the first valve, the second valve, the third valve, and the fourth valve, are independently configurable to change between or among gaseous communication flow paths within the collection system.

21. The system of claim 7, wherein each of the first valve, the second valve, the third valve, and the fourth valve, are independently configurable to be in gaseous communication with He flow meters.

22. The system of claim 7, wherein each of the first valve, third valve, and the fourth valve, are independently configurable to be in gaseous communication with outlet vents.

* * * * *